United States Patent
Voytik-Harbin et al.

(10) Patent No.: US 11,739,291 B2
(45) Date of Patent: Aug. 29, 2023

(54) 3-DIMENSIONAL (3D) TISSUE-ENGINEERED MUSCLE FOR TISSUE RESTORATION

(71) Applicant: Purdue Research Foundation, West Lafayette, IN (US)

(72) Inventors: Sherry L. Voytik-Harbin, Zionsville, IN (US); Stacey L. Halum, Indianapolis, IN (US); Sarah Brookes, West Lafayette, IN (US); Hongji Zhang, Naperville, IL (US)

(73) Assignee: Purdue Research Foundation, West Lafayette, IN (US)

( * ) Notice: Subject to any disclaimer, the term of this patent is extended or adjusted under 35 U.S.C. 154(b) by 365 days.

(21) Appl. No.: 16/607,665

(22) PCT Filed: Apr. 25, 2018

(86) PCT No.: PCT/US2018/029473
§ 371 (c)(1),
(2) Date: Oct. 23, 2019

(87) PCT Pub. No.: WO2018/200750
PCT Pub. Date: Nov. 1, 2018

(65) Prior Publication Data
US 2020/0190466 A1    Jun. 18, 2020

Related U.S. Application Data

(60) Provisional application No. 62/489,849, filed on Apr. 25, 2017.

(51) Int. Cl.
| | | |
|---|---|---|
| *C07K 14/78* | (2006.01) | |
| *C12N 5/00* | (2006.01) | |
| *C12N 5/077* | (2010.01) | |
| *C12N 5/074* | (2010.01) | |

(52) U.S. Cl.
CPC ............ *C12N 5/0068* (2013.01); *C07K 14/78* (2013.01); *C12N 5/0062* (2013.01); *C12N 5/0652* (2013.01); *C12N 5/0696* (2013.01); *C12N 2500/34* (2013.01); *C12N 2533/54* (2013.01)

(58) Field of Classification Search
None
See application file for complete search history.

(56) References Cited

U.S. PATENT DOCUMENTS

| | | |
|---|---|---|
| 3,949,073 A | 4/1976 | Daniels et al. |
| 4,233,360 A | 11/1980 | Luck et al. |
| 4,439,521 A | 3/1984 | Archer et al. |
| 4,544,516 A | 10/1985 | Hughes et al. |
| 4,582,640 A | 4/1986 | Smestad et al. |
| 4,600,533 A | 7/1986 | Chu et al. |
| 4,703,108 A | 10/1987 | Silver |
| 4,743,552 A | 5/1988 | Friedman et al. |
| 4,776,853 A | 10/1988 | Klement et al. |
| 4,789,663 A | 12/1988 | Wallace et al. |
| 4,801,299 A | 1/1989 | Brendel et al. |
| 4,829,000 A | 5/1989 | Kleinman et al. |
| 4,902,508 A | 2/1990 | Badylak et al. |
| 4,912,057 A | 3/1990 | Guirguis et al. |
| 4,956,178 A | 9/1990 | Badylak et al. |
| 5,032,508 A | 7/1991 | Naughton et al. |
| 5,163,955 A | 11/1992 | Love et al. |
| 5,204,382 A | 4/1993 | Wallace et al. |
| 5,266,480 A | 11/1993 | Naughton et al. |
| 5,275,826 A | 1/1994 | Badylak et al. |
| 5,281,422 A | 1/1994 | Badylak et al. |
| 5,336,616 A | 8/1994 | Livesey et al. |
| 5,352,463 A | 10/1994 | Badylak et al. |
| 5,372,821 A | 12/1994 | Badylak et al. |
| 5,420,248 A | 5/1995 | Devictor et al. |
| 5,460,962 A | 10/1995 | Kemp et al. |
| 5,478,739 A | 12/1995 | Sivka et al. |
| 5,518,915 A | 5/1996 | Naughton et al. |
| 5,554,389 A | 9/1996 | Badylak et al. |
| 5,604,106 A | 2/1997 | Liotta et al. |
| 5,641,518 A | 6/1997 | Badylak et al. |
| 5,695,998 A | 12/1997 | Demeter et al. |
| 5,753,267 A | 5/1998 | Badylak et al. |
| 5,863,531 A | 1/1999 | Naughton et al. |

(Continued)

FOREIGN PATENT DOCUMENTS

| | | |
|---|---|---|
| AU | 48841/99 | 3/2000 |
| CA | 2212704 | 8/1996 |

(Continued)

OTHER PUBLICATIONS

JPK Instruments, Collagen: levels of structure and alignment, pp. 1-6, retrieved from the internet Jan. 27, 2022: https://www.jpk.com/app-technotes-img/AFM/pdf/jpk-app-collagen.14-1.pdf (Year: 2022).*
Merriam-Webster, Engineer definition, retrieved from the internet Jan. 27, 2022: https://www.merriam-webster.com/dictionary/engineer (Year: 2022).*
Lee et al Journal of Anatomy (2019) 234, pp. 252-262 (Year: 2019).*
Merriam-Webster: definition of "synthesis", retriefed from the internet, Sep. 1, 2022: https://www.merriam-webster.com/dictionary/synthetic (Year: 2022).*
International Search Report and Written Opinion issued by the ISA/US Commissioner for Patents, dated Jul. 6, 2018, for International Application No. PCT/US2018/029473.

(Continued)

*Primary Examiner* — Evelyn Y Pyla
(74) *Attorney, Agent, or Firm* — Barnes & Thornburg LLP

(57) ABSTRACT

The present disclosure provides solid collagen constructs and tissue compositions, wherein a polymerizable collagen solution or suspension is extruded in the presence or absence of cells to formed an aligned architecture comprising solid collagen constructs such as those made with fibrillar collagen. Methods of using and of manufacturing solid collagen constructs and tissue compositions, where the component collagen is solid fibrillar collagen and cells are preferentially aligned, are also provided.

18 Claims, 15 Drawing Sheets

(56) References Cited

U.S. PATENT DOCUMENTS

| | | |
|---|---|---|
| 5,866,414 A | 2/1999 | Badylak et al. |
| 5,885,619 A | 3/1999 | Patel et al. |
| 5,948,429 A | 9/1999 | Bell et al. |
| 5,955,110 A | 9/1999 | Patel et al. |
| 6,022,743 A | 2/2000 | Naughton et al. |
| 6,087,157 A | 7/2000 | Badylak et al. |
| 6,099,567 A | 8/2000 | Badylak et al. |
| 6,171,344 B1 | 1/2001 | Atala |
| 6,187,039 B1 | 2/2001 | Hiles et al. |
| 6,187,047 B1 | 2/2001 | Kwan et al. |
| 6,206,931 B1 | 3/2001 | Cook et al. |
| 6,241,981 B1 | 6/2001 | Cobb et al. |
| 6,248,587 B1 | 6/2001 | Rodgers et al. |
| 6,264,992 B1 | 7/2001 | Voytik-Harbin et al. |
| 6,358,284 B1 | 3/2002 | Fearnot et al. |
| 6,375,989 B1 | 4/2002 | Badylak et al. |
| 6,379,710 B1 | 4/2002 | Badylak |
| 6,384,196 B1 | 5/2002 | Weis et al. |
| 6,419,920 B1 | 7/2002 | Mineau-Hanschke |
| 6,444,229 B2 | 9/2002 | Voytik-Harbin et al. |
| 6,475,232 B1 | 11/2002 | Babbs et al. |
| 6,485,723 B1 | 11/2002 | Badylak et al. |
| 6,497,875 B1 | 12/2002 | Sorrell et al. |
| 6,576,265 B1 | 6/2003 | Spievack |
| 6,586,493 B1 | 7/2003 | Massia et al. |
| 6,592,623 B1 | 7/2003 | Bowlin et al. |
| 6,592,794 B1 | 7/2003 | Bachrach |
| 6,666,892 B2 | 12/2003 | Hiles et al. |
| 6,682,670 B2 | 1/2004 | Noff |
| 6,793,939 B2 | 9/2004 | Badylak |
| 6,893,812 B2 | 5/2005 | Weltering et al. |
| 6,918,396 B1 | 7/2005 | Badylak et al. |
| 6,962,814 B2 | 11/2005 | Mitchell et al. |
| 7,029,689 B2 | 4/2006 | Berglund et al. |
| 7,087,089 B2 | 8/2006 | Patel et al. |
| 7,175,841 B2 | 2/2007 | Badylak et al. |
| 7,771,717 B2 | 8/2010 | Badylak et al. |
| 7,795,022 B2 | 9/2010 | Badylak |
| 7,815,686 B2 | 10/2010 | Badylak |
| 8,084,055 B2 | 12/2011 | Voytik-Harbin et al. |
| 8,222,031 B2 | 7/2012 | Noll |
| 8,241,905 B2 | 8/2012 | Forgacs et al. |
| 8,343,758 B2 | 1/2013 | Cheema et al. |
| 8,431,158 B2 | 4/2013 | Shoseyov |
| 8,449,902 B2 | 5/2013 | Brown et al. |
| 8,512,756 B2 | 8/2013 | Voytik-Harbin et al. |
| 8,518,436 B2 | 8/2013 | Voytik-Harbin et al. |
| 8,580,564 B2 | 11/2013 | Brown et al. |
| 8,652,500 B2 | 2/2014 | Bosley, Jr. |
| 8,741,352 B2 | 6/2014 | Hodde et al. |
| 9,101,693 B2 | 8/2015 | Brown et al. |
| 9,205,403 B2 | 12/2015 | Dubois |
| 9,707,703 B2 | 7/2017 | Tully |
| 9,744,123 B2 | 8/2017 | Castiglione-Dodd et al. |
| 9,757,495 B2 | 9/2017 | Murray |
| 10,314,940 B2 | 6/2019 | Voytik-Harbin |
| 2002/0076816 A1 | 6/2002 | Dai et al. |
| 2002/0170120 A1 | 11/2002 | Eckmayer et al. |
| 2002/0172705 A1 | 11/2002 | Murphy et al. |
| 2003/0216811 A1 | 1/2003 | Badylak |
| 2003/0113302 A1 | 6/2003 | Revazoa et al. |
| 2003/0216812 A1 | 11/2003 | Badylak |
| 2004/0006395 A1 | 1/2004 | Badylak |
| 2004/0030404 A1 | 2/2004 | Noll et al. |
| 2004/0037813 A1 | 2/2004 | Simpson et al. |
| 2004/0078076 A1 | 4/2004 | Badylak et al. |
| 2004/0137616 A1 | 7/2004 | Isseroff et al. |
| 2005/0014181 A1 | 1/2005 | Galis et al. |
| 2005/0019419 A1 | 1/2005 | Badylak et al. |
| 2005/0153442 A1 | 7/2005 | Katz et al. |
| 2005/0202058 A1 | 9/2005 | Hiles |
| 2005/0226856 A1 | 10/2005 | Ahlfors |
| 2005/0260748 A1 | 11/2005 | Chang et al. |
| 2005/0266556 A1 | 12/2005 | Yoder et al. |
| 2006/0014284 A1 | 1/2006 | Graeve |
| 2006/0134072 A1 | 6/2006 | Pedrozo et al. |
| 2006/0147501 A1 | 7/2006 | Hillas et al. |
| 2006/0165667 A1 | 7/2006 | Laughlin et al. |
| 2006/0235511 A1 | 10/2006 | Osborne |
| 2006/0257377 A1 | 11/2006 | Atala et al. |
| 2007/0026518 A1 | 2/2007 | Healy et al. |
| 2007/0077652 A1 | 4/2007 | Peled et al. |
| 2007/0141037 A1 | 6/2007 | Badylak et al. |
| 2007/0190646 A1 | 8/2007 | Engler et al. |
| 2007/0269476 A1 | 11/2007 | Voytik-Harbin et al. |
| 2008/0025956 A1 | 1/2008 | Yoder et al. |
| 2008/0070304 A1 | 3/2008 | Forgacs et al. |
| 2008/0095815 A1 | 4/2008 | Mao |
| 2008/0107750 A1 | 5/2008 | Hodde et al. |
| 2008/0181935 A1 | 7/2008 | Bhatia et al. |
| 2008/0199441 A1 | 8/2008 | Peled |
| 2008/0220506 A1 | 9/2008 | Yost et al. |
| 2008/0268052 A1 | 10/2008 | Voytik-Harbin et al. |
| 2009/0069893 A1 | 3/2009 | Paukshto et al. |
| 2009/0175922 A1 | 7/2009 | Voytik-Harbin |
| 2009/0269386 A1 | 10/2009 | Zubery et al. |
| 2009/0280180 A1 | 11/2009 | Voytik-Harbin et al. |
| 2009/0324681 A1 | 12/2009 | Badylak |
| 2010/0119578 A1 | 5/2010 | To et al. |
| 2010/0143476 A1 | 6/2010 | March et al. |
| 2010/0272697 A1 | 10/2010 | Naji et al. |
| 2011/0182962 A1 | 7/2011 | McKay |
| 2012/0027732 A1 | 2/2012 | Voytik-Harbin et al. |
| 2012/0094376 A1 | 4/2012 | Voytik-Harbin et al. |
| 2012/0115222 A1 | 5/2012 | Voytik-Harbin et al. |
| 2012/0134949 A1 | 5/2012 | Brown et al. |
| 2012/0141417 A1 | 5/2012 | Voytik-Harbin et al. |
| 2012/0171768 A1 | 7/2012 | Voytik-Harbin et al. |
| 2012/0189588 A1 | 7/2012 | Nahas et al. |
| 2012/0273993 A1 | 11/2012 | Shoseyov et al. |
| 2012/0297550 A1 | 11/2012 | Ngo et al. |
| 2014/0056865 A1 | 2/2014 | Samaniego et al. |
| 2014/0193473 A1 | 7/2014 | Yoder et al. |
| 2014/0193477 A1 | 7/2014 | Chaikof et al. |
| 2015/0105323 A1 | 4/2015 | Novak et al. |
| 2016/0175482 A1 | 6/2016 | Quirk et al. |
| 2018/0050130 A1 | 2/2018 | Jiang et al. |
| 2019/0351097 A1 | 11/2019 | Voytik-Harbin |

FOREIGN PATENT DOCUMENTS

| | | |
|---|---|---|
| DE | 201 15 753 U1 | 1/2002 |
| EP | 0443094 | 8/1991 |
| EP | 1264878 | 12/2002 |
| EP | 1 270 672 A1 | 1/2003 |
| EP | 1 674 116 A2 | 6/2006 |
| GB | 2366736 | 3/2002 |
| JP | 1-247082 A | 10/1989 |
| JP | 6-510927 A | 12/1994 |
| JP | 7-74239 B2 | 8/1995 |
| WO | 92/15676 | 9/1992 |
| WO | 93/00441 | 1/1993 |
| WO | 93/05798 | 4/1993 |
| WO | WO 94/03119 | 2/1994 |
| WO | 94/11008 | 5/1994 |
| WO | 94/23016 | 10/1994 |
| WO | 96/24661 | 8/1996 |
| WO | 97/17038 | 5/1997 |
| WO | 98/52637 | 1/1998 |
| WO | 98/06445 | 2/1998 |
| WO | 98/25637 | 6/1998 |
| WO | 00/15765 | 3/2000 |
| WO | 00/62833 | 10/2000 |
| WO | 01/10355 | 2/2001 |
| WO | WO 2001/023529 | 4/2001 |
| WO | WO 2001/045765 | 6/2001 |
| WO | 01/48153 | 7/2001 |
| WO | 01/78754 | 10/2001 |
| WO | 02/07646 | 1/2002 |
| WO | 02/14480 | 2/2002 |
| WO | 02/20729 | 3/2002 |
| WO | 2002/102237 | 12/2002 |
| WO | 2003/068287 | 8/2003 |
| WO | 2003/071991 | 9/2003 |

(56) References Cited

FOREIGN PATENT DOCUMENTS

| WO | 03/087337 | 10/2003 |
|---|---|---|
| WO | 03/092471 | 11/2003 |
| WO | 03/097694 | 11/2003 |
| WO | WO 04/028404 | 4/2004 |
| WO | 2004/060426 | 7/2004 |
| WO | WO 04/078120 | 9/2004 |
| WO | 2006/003442 | 1/2006 |
| WO | 2006/124946 | 11/2006 |
| WO | WO 2006/125025 | 11/2006 |
| WO | WO 2007/028079 | 3/2007 |
| WO | WO 2007/136634 | 11/2007 |
| WO | WO 2008/036393 | 3/2008 |
| WO | 00/47219 | 8/2008 |
| WO | 2008/124169 | 10/2008 |
| WO | WO 2009/076441 | 6/2009 |
| WO | WO 2010/123928 | 10/2010 |
| WO | WO 2011/009054 | 1/2011 |
| WO | 2012/004564 | 1/2012 |
| WO | 2017/044847 | 3/2017 |
| WO | 2018/144496 | 8/2018 |
| WO | WO 2019/023266 A1 | 1/2019 |

OTHER PUBLICATIONS

Wikipedia, "Oligomer," Sep. 25, 2015, retrieved on Jun. 22, 2018 from https://en.wikipedia.org/w/index.php?title+Oligomer&oldid=682674890.

Wu et al., "Bioprinting three-dimensional cell-laden tissue constructs with controllable degradation," Scientific Reports, 6:24474, Apr. 19, 2016.

Wang et al, Sheng Li Xue Bao, 2005, 57(2): 259-269; Astract Only.

Blay et al., "Epidermal Growth Factor Promotes the Chemotactic Migration of Cultured Rat Intestinal Epithelial Cells," J. Cell Physiology, 1985, 124(1) pp. 107-112.

Boder, G.B., "Mammalian Cell Cultures for Genetically Engineered Products," Toxicologic Pathology, 1989, 17(4) p. 827.

Delcourt-Huard, et al., "Reconstituted Human Gingivial Epithelium: Nonsubmerged In Vitro Model," In Vitro Cellular & Developmental Biology Animal, Jan. 1997, 33(1) p. 30-6.

Grinnel, "Cell-Collagen Interactions: Overview," Methods in Enzymology, 1982, 82, 499-503.

Mikos, A.G., et al., "Islet Transplantation to Create a Bioartificial Pancreas," Biotech. and Bioengineering, 1994, 43, 673-7.

Sato et al., "Artificial Esophagus," Materials Science Forum, 1997, 250, 105-14.

Schor et al., "The Use of Three-Dimensional Collagen Gels for the Study of Tumour Cell Invasion In Vitro: Experimental Parameters Influencing Cell Migration Into the Gel Matrix," Int. J. Cancer, 1982, 29, 57-62.

Abou-Neel et al. "Use of multiple unconfined compression for fine control of collagen gel scaffold and mechanical properties," Soft Matter, 2006, 2, 986-92.

International Preliminary Report on Patentability and Written Report for PCT/US2006/018998; 9 pages.

International Preliminary Report on Patentability and Written Report for PCT/US2006/019130; 8 pages.

International Search Report and Written Opinion for PCT/US2010/042290; 13 pages.

International Search Report and Written Opinion for PCT/US2012040737; 6 pages.

International Search Report and Written Opinion for PCT/US2015/047176; 12 pages.

"Basement Membrane" accessed online at http://en.wikipedia.orq/wiki/Basement_membrane#Composition on Jun. 11, 2010.

"Extracellular Matrix" accessed at http://en.wikipedia.orq/wiki/Extracellular_matrix on Jun. 11, 2010.

Bell, Brett J. et al., "Cell Density and Extracellular Matrix (ECM) Microstructure Control Mechanical Behavior of Engineered Tissue Constructs, *2005 Summer Bioengineering conference*", (Jun. 22-26, 2005).

Bjornsson, S., "Simultaneous Preparation and Quantitation of Proteoglycans by Precipitation with Alcian Blue", Analytical Biochemistry, vol. 210, 1993, pp. 282-291.

Brennan and Davison, "Role of aldehydes in collagen fibrillogenesis in vitro," Biopolymers, vol. 19, 1980, Issue 10, p. 1861-1873.

Brightman et al., "Time-Lapse Confocal Reflection Microscopy of Collagen Fibrillogenesis and Extracellular Matrix Assembly In Vitro", *Biopolymers*, vol. 54, 222-234, (2000).

Callister, W. D, Jr., Materials Science and Engineering: an Introduction. $3^{rd}$ edition, New York, NY, John Wiley & Sons. Inc., 1994.

Chandrakasan et al. J. Biol. Chem., 1976, 251:6062-67.

Ciovacco et al., Bone, 2009, 44(1):80-86.

Comper, W. D., and A. Veis, "Characterization of Nuclei in in Vitro Collagen Fibril Formation", Biopolymers, vol. 16, 1977, pp. 2133-2142.

Compston, "Bone marrow and bone: a functional unit," Journal of Endocrinology, 173: 387-394, 2002.

Davis, et al., "Injectable Self-Assembling Peptide Nanofibers Create Intramyocardial Microenvironments for Endothelial Cells", *Circulation*, 111, 442-50, (Feb. 1, 2005).

Fulzele, S. V., P. M. Satturwar, A. K. Dorle, "Study of the Biodegradation and in Vivo Biocompatibility of Novel Biomaterials", European Journal of Pharmaceutical Sciences, vol. 20, 2003, pp. 53-61.

Gallop, P. M., and S. Seifter, "Preparation and Properties of Soluble Collagens", Soluble Collagens, 1963, pp. 635-641.

Gelman et al., "Collagen Fibril Formation in Vitro," J. Biol. Chem., 1979, 254(22): 11741-11745.

Gelman et al., "Collagen Fibril Formation," J. Biol. Chem., 1979, 254(1):180-186.

Griffey, S., N. D. Schwade, C. G. Wright, "Particulate Dermal Matrix as an Injectable Soft Tissue Replacement Material", J. Biomed. Mater. Res. vol. 58, 2001, pp. 10-15.

Hou, et al., "Radiolabeled Cell Distribution After Intramyocardial, Intracoronary, and Interstitial Retrograde Coronary Venous Delivery", *Circulation*, 112, 150-6, (Aug. 30, 2005).

Hunt, T. K., P. Twomey, B. Zederfeldt, and J. E. Dunphy, "Respiratory Gas Tensions and PH In Healing Wounds", American Journal of Surgery, vol. 114, 1967, pp. 302-307.

Ingram, D. A., et al., "Identification of a Novel Hierarchy of Endothelial Progenitor Cells Using Human Peripheral and Umbilical Cord Blood", Blood, 104, 2752-2760, (2004).

International Search Report for International Application No. PCT/US07/020463, dated Feb. 21, 2008, 6 pgs.

International Search Report/Written Opinion for PCT/US2007/011681 completed Nov. 6, 2007.

Kacena et al., J. of Histotechnology, 2004, 27:119-130.

Knott et al., "Collagen Cross-Links in Mineralizing Tissues: A Review of Their Chemistry, Function, and Clinical Relevance," 1998, 22(3):181-187.

Kondo et al., "Biology of Hematopoietic Stem Cells and Progenitors: Implications for Clinical Application," Annu. Rev. Immunol., 2003, 21:759-806.

Korff et al., Jour. of Cell Science, vol. 112: 3249-3258 (1999).

Kreger et al., "Hyaluronan concentration within a 3D collagen matrix modulates matrix viscoelasticity, but not fibroblast response," Matrix Biol., 2009, 28(6):336-46.

Kreger, "Design of 3D Collagen Matrices for Cell Delivery and Guidance in Tissue Engineering," Thesis Submitted to the Faculty of Purdue University in Partial Fulfillment of the Requirements for the Degree of Doctor of Philosophy, May 2009, Purdue University.

Lin et al., "Comparison of Physical-Chemistry Properties of Type 1 Collagen from Different Species," *Food Chemistry*, 99(2): 244-251 (2005).

Malvern, *Introduction to the Mechanics of a Continuous Medium*. Upper Saddle River, NJ: Prentice-Hall, 1969.

Marotta, M., G. Martino, "Sensitive Spectrophotometric Method for the Quantitative Estimation of Collagen", Analytical Biochemistry, vol. 150, 1985, pp. 86-90.

Miller et al., "Preparation and Characterization of the Different Types of Collagen," *Methods in Enzymology*, 82: 33-64 (1982).

(56) References Cited

OTHER PUBLICATIONS

Miller, E. J., E. H. Epstein, Jr., and K. A. Piez, "Identification of three Genetically Distinct Collagens by Cyanogen Bromide Cleavage of Insoluble Human Skin and Cartilage Collagen", Biochemical and Biophysical Research Communications, vol. 42, No. 6, 1971, pp. 1024-1029.
Na, "Monomer and Oligomer of Type I Collagen: Molecular Properties and Fibril Assembly," *Biochemistry*, 1989, 28(18):7161-7167.
Narmoneva et al., "Endothelial Cells Promote Cardiac Myocyte Survival and Spatial Reorganization", *Circulation*, 110, 962-968, (Aug. 24, 2004).
Nguyen et al., "Comparison of the Amino Acid Composition of Two Commercial Porcine Skins (Rind)," *Journal of Agricultural and Food Chemistry*, 34(3): 565-572 (1986).
Nielsen, T. B. and J. A. Reynolds, "Measurements of Molecular Weights by Gel Electrophoresis", Methods in Enzymology, vol. 48, Hirs and Temasheff, Eds., Academic Press, New York, 1978, pp. 3-10.
Orschell-Traycoff et al., Blood, 2000, 96:1380-1387.
Osborne, et al., "Investigation into the tensile properties of collagen/chondroitin-6-sulphate gels: the effect of crosslinking agents and diamines", *Medical & Biological Engineering & Computing*, vol. 36, 129-134, (1998).
Ozerdem, et al., "Physical Response of Collagen Gels to Tensile Strain", *Journal of Biomechanical Engineering*, vol. 117, 397-401, (Nov. 1995).
Pizzo et al., "Cell-Extracellular Matrix (ECM) Micro-Mechanical Behavior Depends on ECM Microstructure and Cell Type", *2005 Summer Bioengineering Conference*, (Jun. 22-26, 2005).
Pizzo et al., "Extracellular matrix (ECM) microstructural composition regulates local cell-ECM biomechanics and fundamental fibroblast behaviour: a multidimensional perspective", *J Appl Physiol*, 98: 1909-1921, (2005).
Pizzo et al., "Long-term Production of Choline Acetylatransferase in the CNS After Transplantation of Fibroblasts Modified with a Regulatable Vector", *Mol Brain Res*, 126, 1-13 (2004).
Rehman, et al., "Secretion of Angiogenic and Antiapoptotic Factors by Human Adipose Stromal Cells", *Circulation*, 109: 1292-8, (Mar. 16, 2004).
Reinlib, et al., "Cell Transplantation as Future Therapy for Cardiovascular Disease?", *Circulation*, 101: e182-e187, (2000).
Roeder B. A., K. Kokini, J. E. Sturgis, J. P. Robinson, S. L. Voytik-Harbin, "Tensile Mechanical Properties of Three-Dimensional Type 1 Collagen Extracellular Matrices with Varied Microstructure", J. Biomech. Eng., vol. 124, 2002, pp. 214-222.
Roeder et al., "Local, Three-Dimensional Strain Measurements Within Largely Deformed Extracellular Matrix Constructs", *J Biomech Eng*, 126, 699-708, (2004).
Scadden, "The stem cell niche as an entity of action," Nature, 441: 1075-1079, 2006.
Schechner et al., "In vivo formation of complex microvessels lined by human endothelial cells in an immunodeficient mouse," *PNAS*, Aug. 1, 2000, vol. 97, No. 16, 9191-9196.
Schilling, J. A., W. Joel, H. M. Shurley, "Wound Healing: A Comparative Study of the Histochemical Changes in Granulation Tissue Contained in Stainless Steel Wire Mesh and Polyvinyl Sponge Cylinders", Surgery, vol. 46, No. 4, Oct. 1959, pp. 702-710.
Shiozawa et al., "The bone marrow niche: habitat to hematopoietic and mesenchymal stem cells, and unwitting host to molecular parasites," Leukemia, 22(5): 941-950, 2008.
Sieminski et al., Expt. Cell Res., vol. 297, pp. 574-584 (2004).
Spradling et al., "Stem Cells Find Their Niche," Nature, 414: 98-104, 2001.
Strang, et al., *Linear Algebra and Its Applications*. 3rd edition. San Diego, CA: Academic Press, 1988.
Sykes, B., B. Puddle, M. Francis, and R. Smith, "The Estimation of Two Collagens from Human Dermis by Interrupted Gel Electrophoresis", Biochemical and Biophysical Research Communications, vol. 72, No. 4, 1976, pp. 1472-1480.
Veis, Arthur, et al., "Fundamentals of Interstitial; Collagen Self-Assembly", 1994, Extracellular Matrix Assembly and Structure, Academic Press, pp. 15-45.
Voytik-Harbin et al., "Application and Evaluation of the Alamarblue Assay For Cell Growth and Survival of Fibroblasts", *In Vitro Cell Dev Biol Anim*, 34, 239-246, (1998).
Voytik-Harbin et al., "Simultaneous Mechanical Loading and Confocal Reflection Microscopy for Three-Dimensional Microbiomechanical Analysis of Biomaterials and Tissue Constructs", *Microsc Microanal*, 9, 74-85, (2003).
Voytik-Harbin et al., Small Intestinal Submucosa: A Tissue-Derived Extracellular Matrix That Promotes Tissue-Specific Growth and Differentiation of Cells in Vitro, *Tissue Engineering*, 4, 2, 157-174, (1998).
Voytik-Harbin et al., "Three-Dimensional Imaging of Extracellular Matrix and Extracellular Matrix-Cell Interactions", *Methods In Cell Biology*, 63, 583-597, (2001).
Wess, Collagen fibrillar structure and hierarchies in P. Fratzl (ed.), Collagen: Structure and Mechanics, Springer Science + Business Media, LLC, New York, 2008, 53-60.
Yoder et al., "Redefining endothelial progenitor cells via clonal analysis and hematopoietic stem/progenitor cell principals," *Blood*, 2007, 109:1801-1809.
International Search Report and Written Opinion for PCT/US2008/086232, dated Jan. 16, 2009, 12 pages.
Bailey JL et al., "Collagen Oligomers Modulate Physical and Biological Properties of Three-Dimensional Self-Assembled Matrices," Biopolymers, 2010; 95(2): 77-93.
Na et al., "In Vitro Collagen Fibril Assembly in Glycerol Solution: Evidence for a Helical Cooperative Mechanism Involving Microfibrils," Biochemistry, 1986; 25: 958-966.
Na et al., "Mechanism of in Vitro Collagen Fibril Assembly," Journal of Biological Chemistry, 1986; 261(26): 12290-12299.
Voytik-Harbin et al., "Identification of Extractable Growth Factors from Small Intestine Submucosa," J Cell. Biochemistry, 1997; 67: 478-491.
Condell RA et al., "Analysis of Native Collagen Monomers and Oligomers by Size-Exclusion High-Performance Liquid Chromatography and its Application," *Analytical Biochemistry*, 1993; 212: 436-445.
"Density" from Merriam-Webster online, accessed on Feb. 1, 2011.
Brandner et al., "replicating the Hematopoietic Stem Cell Niche," Purdue University, BME Graduate Student Association Research Symposium, Poster Presentation, Jul. 16, 2009.
Whittington et al., "Collagen oligomers modulate physical and cell-instructive properties of polymerizable collagen matrices," Biomaterials Day Society for Biomaterials, Nov. 6, 2010 (PowerPoint presentation and poster).
Kreger et al., "Polymerization and matrix physical properties as important design considerations for soluble collagen formulations," 2010, Biopolymers, 93(8): 690-707.
Critser et al., "Collagen matrix physical properties modulate endothelial colony forming cell-derived vessels in vivo," 2010, Microvasc. Res., 80(1): 23-30.
Munakata, et al., Glycobiology, vol. 9, 1023-1027 (1999).
Kim, "Characterization of Acid-soluble Collagen from Pacific Whiting Surimi Processing Byproducts," J. Food Science, 2004, 69: C637-C642.
Billiar, Cellular and Biomolecular Mechanics and Mechanobiology, Amit Gefen, Ed., p. 210 (2011).
Ho et al., "Characterization of Collagen Isolation and Application of Collagen Gel as a Drug Carrier", J. of Controlled Release, vol. 44, pp. 103-112 (1997).
Liu, Asian-Aust J. Anim. Sci, 2001; 14(11):1638-1644.
Lynn et al., "Antigenicity and immunogenicity of collagen," J Biomed Mater Res, Part B: Appl Biomater, 2004; 71B: 343-354.
Taichman et al., "Human Osteoblasts Support Hematopoiesis through the Production of Granulocyte Colony-stimulating Factor," Journal of Experimental Medicine, 1994; 179:1677-1682.
TeBmar et al., "Hydrogels for tissue engineering," *Fundamentals of Tissue Engineering and Regenerative Medicine*, 2009; p. 495-517.
Koken, "About Collagen," Technical information, Support webpage, 2006.

(56) References Cited

OTHER PUBLICATIONS

Taqvi et al., "Influence of scaffold physical properties and stromal cell coculture on hematopoietic differentiation of mouse embryonic stem cells," *Biomaterials*, 2006; 24:6024-6031.
Engler et al., "Matrix elasticity directs stem cell lineage specification," *Cell*, 2006; 126:677-689.
Young, et al., "Adult Stem Cells." Anat. Record Pt. A: Disc. Mol. Cell. Evol. Biol. 276A:75-102 (2004).
Yang, et al., "The application of recombinant human collagen in tissue engineering." *Biodrugs* 18:103-119 (2004).
Fischbach, et al., "Three-dimensional in vitro model of adipogenesis: coparison of culture conditions." *Tissue Engineering* 10:215-229 (2004).
Reinisch et al., "Humanized large-scale expanded endothelial colony-forming cells function in vitro and in vivo," *Blood*, 2009; 113:6716-6725.
Silver et al., "Collagen self-assembly and the development of tendon mechanical properties," *Journal of Biomechanics*, 2003; 36:1529-1553.
Product information: Collagen Solution—Type I from rat tail, Sigma, http://www.siqmaaldrich.com/etc/medialib/docs/Siqma/Datasheet/3/c3867dat.Par.0001.File.tmp/c3867dat.pdf.
Gallagher D, "Stem cells being made from blood," available at www.bbc.co.uk/news/health-20539835.
Ingram D et al., "Vessel wall-derived endothelial cells rapidly proliferate because they contain a complete hierarchy of endothelial progenitor cells," *Blood*, 2005; 105(7):2783-6 (Epub Dec. 7, 2004).
Ingram D et al., "Unresolved questions, changing definitions, and novel paradigms for defining endothelial progenitor cells via clonal analysis and hematopoietic stem/progenitor cell principals," *Blood*, 2007; 109(5):1801-9 (Epub Oct. 19, 2006).
Prater DN et al., "Working hypothesis to redefine endothelial progenitor cells," *Leukemia*, 2007; 21(6):1141-9 (Epub Mar. 29, 2007).
Case J et al., "Human CD34+AC133+VEGFR-2+ cells are not endothelial progenitor cells but distinct, primitive hematopoietic progenitors," *Exp Hematol.*, 2007; 35(7):1109-18.
Hirschi KK et al, "Assessing identify, phenotype, and fate of endothelial progenitor cells," *Arterioscler Thromb Vasc Biol*, 2008; 28(9):1584-95 (Epub Jul. 31, 2008).
Timmermans F et al., "Endothelial progenitor cells: identify defined?", *J Cell Mol Med*, 2009; 13(1):87-102.
Mund JA et al., "Endothelial progenitor cells and cardiovascular cell-based therapies," *Cytotherapy*, 2009; 11(2):103-13.
Chor Wing Tam et al. EWMA Journal, 2012; 12(2).
Boyd et al. Atlas and Text of Corneal Pathology and Surgery; 2011 [Document Rejected by Exam. because illegible].
Stem Cell Differentiation (science and global issues/biology, cell biology), 2013.
Shimizu, "Fabrication of pulsatile cardiac tissue grafts using a novel 3-dimensional cell sheet manipulation technique and temperature-responsive cell culture surfaces," *Circ Res.*, 2002, 90:e40-48.
Mizuno et al., "Osteogenesis by bone marrow stromal cells maintained on type 1 collagen matrix gels in vivo." Bone 20:101-107 (1997).
Young et al., "Use of meschymal stem cells in a collagen matrix for Achilles tendon repair. J. Ortopaedic Res. 16" 406-413 (1998).
Vasiliev and Gelfand, Neoplastic and Normal Cells in Culture, Cambring University Press, p. 19, 1981.
"Stem Cells and the future of Regenerative Medicine" published by National Academy of Sciences, p. 19, 2002.
McBeath et al., "Cell shape, cytoskeletal tension, and RhoA regulate stem cell lineage commitment," *Developmental Cell*, 2004; 6:483-495.
Engler et al., "Myotubes differentiate optimally on substrates with tissue-like stiffness: pathological implications for soft or stiff microenvironments," *Journal of Cell Biology*, 2004; 165:877-887.
Kong et al., "FRET measurements of cell-traction forces and nano-scale clustering of adhesion ligands varied by substrate stiffness," *PNAS*, 2005; 102:4300-4305.
Settleman, "Tension Precedes Commitment—Even for a Stem Cell," *Molecular Cell*, 2004; 14:148-150.
Engler et al., "Substrate elasticity directs adult mesenchymal stem cell differentiation," Abstract 783, The 37th Middle Atlantic Regional Meeting, May 2005.
Williams et al, 1978, Journ Biol Chem, 253: 6578-6585.
Huang et al, 2005, Mechanisms and Dynamics of Mechanical Strengthening in Ligament-Equivalent Fibroblast-Populated Collagen Matrices, Annals of Biomedical Engineering, 21: 289-305.
Rucha Joshi: "Purdue e-Pubs Open Access Dissertations Theses and Dissertations Designer Collagen-Fibril Biograft Materials for Tunable Molecular Delivery," Jan. 1, 2016 https://docs.lib.purdue.edu/open_access_dissertations/1218.
"Artificial Blood Vessel," English translation of Japanese Patent Application Publication No. 3-12169, 1991, 16 pages.
Asem, E.K. et al. "Basal lamina of Avian Ovarian Follicle: Influence On Morphology of Granulosa Cells In-Vitro," Comparative Biochemistry and Physiology, Part C, 125 (2000), pp. 189-201.
Asem, E.K. et al. "Effect of Basal Lamina on Progesterone Production by Chicken Granulosa Cells In Vitro—Influence of Follicular Development," Comparative Biochemistry and Physiology, Part C, 125 (2000) pp. 233-244.
Campbell, J.H. et al. "Endothelial Cell Influences on Vascular Smooth Muscle Phenotype," Ann. Rev. Physiol., 1986, vol. 48, 384-91.
Nugent, H.M. et al. "Endothelial Implants inhibit Intimal Hyperplasia After Porcine Angioplasty," Circulation Research, Mar. 5, 1999, 84(4) pp. 384-391.
Hirschi, K.K. et al. "PDGF, TGF-β, and Heterotypic Cell-Cell Interactions Mediate Endothelial Cell-Induced Recruitment of 10T1/2 Cells and Their Differentiation to a Smooth Muscle Fate," The Journal of Cell Biology, 1998, 141(3) pp. 805-814.
Badylak, S.T., et al. "Endothelial Cell Adherence to Small Intestinal Submucosa: An Acellular Bioscaffold," Biomaterials, 1999, 20, pp. 2257-2263.
Bell, et al., "Production of a tissue-like structure by contraction of collagen lattices by human fibroblasts of different proliferative potential in vitro," Mar. 1979, Proc. Natl. Sci. USA, 76(3) pp. 1274-1278.
Bhatia, S.N. et al., "Controlling Cell Interactions by Micropatterning in Co-Cultures: Hepatocytes and 3T3 Fibroblasts," Journal of Biomedical Materials Research, 1997, 34, pp. 189-199.
Boder, G.B. and Hull, R.H., "Introduction to Techniques in Mammalian Cell Culture," Manual of Industrial Microbiology and Biotechnology, 1983, Ed. A.L. Demain and N.A. Solomon, pp. 248-262.
Castano, E., et al., "Inhibition of DNA Synthesis by Aspirin in Swiss 3T3 Fibroblasts," Journal of Pharmacology and Experimental Therapeutics, 1997, 280(1) p. 366-72.
Deluca, et al., "Evidence That Human Oral Epithelium Reconstituted In Vitro and Transplanted on Patients with Defects in the Oral Mucosa Retains Properties of the Original Donor Site," Transplantation, 1990, 50(3) p. 454-9.
Elsdale and Bard, "Collagen Substrata for Studies on Cell Behavior," The Journal of Cell Biology, 1972, 54, p. 626-37.
Emerman et al., "Maintenance and Induction of Morphological Differentiation in Dissociated Mammary Epithelium on floating Collagen Membranes," In Vitro, 1977, 13(5) pp. 316-328.
Freed et al., "Joint Resurfacing Using Allograft Chondrocytes and Synthetic Biodegradable Polymer Scaffolds," J. Biomedical Materials Res., 1994, 28, p. 891-9.
Freeman et al., "In vivo-like growth of human tumors in vitro," Proc. Natl. Acad. Sci. USA, Apr. 1986, 83, 2694-8.
Freshney, R.I., "Culture of Animal Ceils: A Manual of Basic Technique," Chapters 12 and 13, Alan R. Liss. Inc., New York (1994) p. 119-43.
Girasole et al., "17-β Estradiol Inhibits IL-6 Production by Bone Marrow-Derived Stromal Cells and osteoblasts In Vitro: A Potential Mechanism for the Antiosteoporotic Effects of Estrogens," The Journal of Clinical Investigation, Inc. 1992, 89,—883-91.
Hayashi, "The effect of three-dimensional structure of extracellular matrix on cellular functions including response to growth factors," Biophysics, 1992, 32(4) p. 211-5.

(56) References Cited

OTHER PUBLICATIONS

Ho, M., et al., "Identification of Endothelial Cell Genes by Combined Database Mining and Microarray Analysis," Physiol. Genomics, 2003, 13, 249-62.
Ibrahiem, E.I.H., et al. "Orthotopic Implantation of Primary N-[4-(5-Nitro-2-furyl)-2-thiazolyl]formamide-induced Bladder Cancer in Bladder Submucosa: An Animal Model for Bladder Cancer Study," Cancer Research, 1983, 43, 617-20.
Kashtan, H. et al., "Intra-rectal injection of tumor cells: a novel animal model of rectal cancer," Surgical Oncology, 1992, 1, 251-6.
Keyes, K. et al. "An In Vitro Tumor Model: Analysis of Angiogenic Factor Expression after Chemotherapy," Cancer Research, 2002, 62, 5597-602.
Kleinman, et al., "Preparation of Collagen Substrates for Cell Attachment: Effect of Collagen Concentration and Phosphate Buffer," Analytical Biochemistry, 1979, 94, 308-12.
Kleinman, et al., "Membrane Complexes with Biological Activity," Biochemistry, 1986, 25, 312-8.
Kubota, Y. et al., "Role of Laminin and Basement Membrane in the Morphological Differentiation of Human Endothelial Cells into Capillary-like Structures," Journal of Cell Biology, 1988, 107, 1589-98.
Kuo, C.Y., et al., "Formation of Pseudoislets from Human Pancreatic Cultures," Pancreas, 1992, 7(3) 320-5.
Lee, et al., "Modulation of Secreted Proteins of Mouse Mammary Epithelial Cells by the Collagenous Substrata," The Journal of Cell Biology, 1984, 98, 146-55.
Liu, C. H., et al., "Effects of Salvianolic Acid-A on NIH/3T3 Fibroblast Proliferation, Collagen Synthesis and Gene Expression," World J. Gastroentero, 2000, 6(3) 361-4.
Maru et al., "An Oncogenic Form of the Flt-1 Kinase has a Tubulogenic Potential in a Sinusoidal Endothelial Cell Line," European Journal of Cell Biology, 2000, 79, 130-43.
Michalopoulos & Pitot, "Primary Culture of Parenchymal Liver Cells on Collagen Membranes," Experimental Cell Research, 1975, 94, 70-8.
Mokonjimobe et al., "Hexosaminidase and alkaline phosphatase activities in articular chondrocytes and relationship to cell culture conditions," Experientia, 1992, 48(4) 396-8.
Nerem, R., "Tissue Engineering: The Hope, The Hype and The Future," Tissue Engineering, 2006, 12(5) 1143-50.
Saltzman et al., "Three-dimensional Cell Cultures Mimic Tissues," Ann. N.Y. Acad. Sci., 1992, 665, 259-73.
Shields et al., Invasion of Collagen Gels by Mouse Lympoid Cells, Immunology, 1984, 51, 259-68.
Takahashi, et al., "Compressive force promotes Sox9, type II collagen and aggrecan and inhibits IL-1β expression resulting in chondrogenesis in mouse embryonic limb bud mesenchymal cells." Journal of Cell Science, 1998, 111(14) 2067-76.
Vescoi et al., "In vivo-like drug responses of human tumors growing in three-dimensional gel-supported primary culture," Proc. Natl. Acad. Sci. USA, 1987, 84, 5029-33.
Wakitani et al., "Mesenchymal Cell-Based Repair of Large, Full Thickness Defects of Articular Cartilage," J. Bone Joint Surg. Am., Abstract, 1994, 76(4) 579-92.
Yang, E.K. et al., "Tissue Engineered Artificial Skin Composed of Dermis and Epidermis," International Society for Artificial Organs, 2000, 24(1) 7-17.
Friess, "Collagen-biomaterial for drug delivery," European Journal of Pharmaceutics and Biopharmaceutics, 1998, 45(2) 113-36.
Ruszczak et al., "Effect of collagen matrices on dermal wound healing," Advanced drug Delivery Reviews, 2003, 55, 1595-611.
Lillie et al., "Growth of Stratified Squamous Epithelium on Reconstituted Extracellular Matrices: Long-Term Culture," Journal of Investigative Dermatology, 1988, 90(2) 100-9.
Silver et al., "Type 1 Collagen in Solution," The Journal of Biological Chemistry, 1980, 19(10) 9427-33.
Glowacki, J. and Mizuno, S. "Collagen Scaffolds for Tissue Engineering," Biopolymers, 2007, 89, 338-44.

Sweeney, et al. "Defining the domains of type I collagen involved in heparin-binding and endothelial tube formation," Proceedings of the National Academy of Science, USA 1998, 95, 275-80.
Volpi et al. "On adaptive structures of the collagen fibrils of bone and cartilage," J. Biomech, 24 (Suppl 1), 1991, 67-77, abstract only.
Zhu et al., "Designed composites for mimicking compressive mechanical properties of articular cartilage matrix," Journal of the Mechanical Behavior of Biomedical Materials, 2014, 36, 32-46.
Mienaltowski, et al. "Structure, Physiology, and Biochemistry of Collagens," Advances in Experimental Medicine and Biology, 2014, 802, 5-29.
Whittington, C., et al., "Oligomers Modulate Interfibril Branching and Mass Transport Properties of Collagen Matrices," Microsc Microanal, Oct. 2013, 19(5) 20 pages.
Shoulders, et al. "Collagen Structure and Stability," Annu. Rev. Biochem., 2009, 78, 929-58.
Blum, K.M., et al., "Acellular and high-density, collagen-fibril constructs with suprafibrillar organization," Biomaterials Science, The Royal Society of Chemistry, 2016, 4, 711-23.
Whittington, C.F., et al., "Collagen-Polymer Guidance of Vessel Network Formation and Stabilization by Endothelial Colony Forming Cells In Vitro," Macromolecular Bioscience, 2013, 13, 1135-49.
Brown, et al., "Ultrarapid Engineering of Biomimetic Materials and Tissues: Fabrication of Nano- and Microstructures by Plastic Compression," Advanced Functional Materials, 2005, 15, 1762-70.
Chicatun, et al., "Osteoid-Mimicking Dense Collagen/Chitosen Hybrid Gels," BioMacromolecules, 2011, 12, 2946-56.
Zorlutuna et al., "Nanopatterning of Collagen Scaffolds Improve the Mechanical Properties of Tissue Engineered Vascular Graft," Biomacromolecules, 2009, 10, 814-21.
Caves, et al., "Elastin-linke protein matrix reinforced with collagen microfibers for soft tissue repair," Biomaterials, 2011, 32(23) 5371-9.
Shepard, et al., "Effect of fiber crosslinking on collage-fiber reinforced collagen-chondroitin-6-sulfate materials for regenerating load-bearing soft tissues," Journal of Biomedical Materials Research, 2012, 101(1) 176-84.
Hambli et al., "Physically based 3D finite element model of a single mineralized collagen microfibril," Journal of Theoretical Biology, 2012, 301, 28-41.
Ji et al., "Mechanics of electrospun collagen and hydroxyapatite/collagen nanofibers," Journal of the Mechanical behavior of Biomedical Materials, 2012, 13, 185-93.
Grover, et al., "Crosslinking and composition influence the surface properties, mechanical stiffness and cell reactivity of collagen-based films," Acta Biomater, 2012, 8(8) 3080-90.
Kuo Ching Chao et al., "A Novel Human Stem Cell Coculture System that Maintains the Survival and Function of Culture Islet-Like Cell Clusters," Cell Transplantation, Jun. 1, 2008, 657-64.
International Preliminary Report on Patentability received for PCT Patent Application No. PCT/US2018/029473, dated Nov. 7, 2019 9 pages.
Sarah Brookes et al: "Three-dimensional tissue-engineered skeletal muscle for laryngeal reconstruction : 3D Tissue Engineered Skeletal Muscle", The Laryngoscope, vol. 128, No. 3, Aug. 26, 2017 (Aug. 26, 2017), pp. 603-609.
Boder G.B. et al. "Long-Term Production of Insulin by Isolated Rabbit Pancreatic Islets in Suspension Culture," J. Cell Biol. 1968, 39(16a).
Backer, M.P., et al. "Large Scale Production of Monoclonal Antibodies in Suspension Culture," Biotechnology and Bioengineering, 1988, 32, pp. 993-1000.
Badylak, S.T., et al. "Directed Connective Tissue Remodeling, Upon a Biologic Collagen Substrate," J. Cell Biochem. 1992, Supplement 16F, Abstract No. CE 027, p. 124.
Bioartificial Organs, Richard Skalak and Fred Fox, eds. Tissue Engineering, Chapter V. Transplants and Artificial Organs, pp. 209, 211-39, and 241-2 (Alan R. Liss, Inc. 1988).
Block, S., "Peroxygen Compounds," Disinfection, Sterilization and Preservation, 4th Edition 1991, pp. 167-181, Phildelphia, Lea, & Febiger.
Boder, G.B., et al. "Visible Light Inhibits Growth of Chinese Hamster Ovary Cells," European J. Cell Biol., 1983, 31, pp. 132-6.

(56) References Cited

OTHER PUBLICATIONS

Boder G.B., et al. "Extended Production of Insulin by Isolated Rabbit Pancreatic Islets; Evidence for Biosynthesis of Insulin," Proc. Soc. Exptl. Biol. Med., 1969, 131, p. 507-13.

Boder, G.B., et al. "Long Term Monolayer Cultures of Islet Cells from Neonatal Mice," J. Cell Biol., 1973, 59, p. 29a.

Denton, G.W., "Chlorhexidine," Disinfection, Sterilization and Preservation, 4th Edition 1991, Philadelphia, Lea, & Febiger, p. 274-89.

Junnosuke, "Tissue culture—Basics and Applications-," Asakura Publishing Co., Ltd., 1965, p. 31.

Kuo C.Y., et al., "Biohybrid Islet-Gland Equivalent for Transplantation," Journal of Cellular Biochemistry, Supplement 18C PZ110, Feb. 13-26, 1994.

Larsson, L. et al., "Changes in the Islets of Langerhans in the Obese Zucker Rat," Lab. Invest. 1977, 36, 593-8.

Francis, et al. "Endothelial cell-matrix interactions in neovascularization," Tissue Engineering Part B: Reviews, 2008, 14(1) 19-32.

Mitra, et al., "Preparation and characterization of malonic acid cross-linked chitosan and collagen 3D scaffolds: an approach on non-covalent interactions," J. Mater. Sci Mater Med, 2012, 23, 1309-21.

Gallop, P. M., and S. Seifter, "Preparation and Properties of Soluble Collagents," Soluble Collagens, 1963, pp. 635-641.

Fogolia, et al. "A new method for the preparation of biocompatible silica coated-collagen hydrogels," J. Mater. Chem. B., 2013, vol. 1, pp. 1283-1290.

Stephens, et al., "Oligomeric collagen as an encapsulation material for islet/beta-cell replacement: effect of islet source, dose, implant site, and administration format," Am. J. Physiol. Endocrinol. Metab., 2020, vol. 319, pp. E388-E400.

Brasack, et al. "Biocompatibility of Modified Silica-Protein Composite Layers," Journal of Sol-Gel Science and Technology, 2000, vol. 19, pp. 479-482.

Xi, et al. "Pore size and pore-size distribution control of porous silica," Sensors and Actuators, 1995, vol. B 24-25, pp. 347-352.

Wilson, et al. "A fibril-reinforced poroviscoelastic swelling model for articular cartilage," Journal of biomechanics, 2005, 38(6) pp. 1195-1204.

Novak et al. "Mechanisms and Microenvironment Investigation of Cellularized High Density Gradient Collagen Matrices via Densification" Adv Funct Mater. Apr. 25, 2016; 26(16): 2617-2628.

Blum et al., "Acellular and Cellular High-Density, Collagen-Fibril Constructs with Suprafibrillar Organization", Biomaterials Science, The Royal Society of Chemistry, 2016, 4, 711-723.

\* cited by examiner

3-DIMENSIONAL (3D) TISSUE-ENGINEERED MUSCLE FOR TISSUE RESTORATION

CROSS-REFERENCE TO RELATED APPLICATIONS

The present application is a U.S. national stage under 35 U.S.C. § 371 of International Application No. PCT/US2018/029473, filed Apr. 25, 2018, which claims the benefit of and priority to U.S. Provisional Application No. 62/489,849, filed Apr. 25, 2017, the entire disclosures of which are expressly incorporated herein by reference in their entireties.

GOVERNMENT RIGHTS

This invention was made with government support under DC014070 awarded by the National Institutes of Health. The government has certain rights in the invention.

FIELD OF INVENTION

This disclosure relates to tissue restoration applications including compositions for such applications and methods for making such compositions. This disclosure includes tissue-engineered solid collagen constructs that may be made with, or without, cells used for tissue restoration as well as an in-vitro testing platform.

BACKGROUND

It has been shown that significant muscular injuries result in a reparative inflammatory-mediated healing response yielding fibrotic scar and dysfunctional muscle. For example, compromised laryngeal function, whether due to congenital malformations, trauma, cancer, or surgical defects, affects thousands of individuals worldwide each year[1]. Unfortunately, therapeutic options to restore lost muscle and dynamic laryngeal functions for these patients are limited. As a result, patients suffer devastating quality of life consequences, including severe voice impairment, an ineffective or unsafe swallow, or airway obstruction, often-necessitating gastrostomy and/or tracheostomy tubes. Advanced tissue engineering and regenerative strategies aimed to develop skeletal muscle implants may provide clinicians with new tools and therapeutic strategies for treating these patients.

Normal skeletal muscle reveals an intricate tissue design, including muscle fibers with their associated contractile machinery and a rich neurovascular supply which is essential for inducing and sustaining dynamic contraction. Furthermore, muscle extracellular matrix (ECM), which includes fibrillar type I collagen as a major component, plays an important role in guiding the muscle-nerve-vascular interface as well as supporting muscle's mechanical function, adaptability, and repair[4]. Therefore, it is not surprising that the majority of muscle engineering approaches focus on capturing these essential design features. At present, the most widely used cell source for engineering skeletal muscle is the putative muscle progenitor cell (MPC; satellite cell), which can be readily isolated from muscle biopsies and cultured to produce myoblasts[5]. MPC can be further modified to induce differentiation and expression of motor endplates, generating motor endplate expressing MPCs, referred to hereafter as MEE. In turn, these cells are interfaced with a variety of natural and synthetic biomaterials, designed to promote myoblast fusion, differentiation, and maturation in vitro or in vivo.

To achieve meaningful therapeutic benefit, it has been proposed that engineered muscle should i) be constructed from autologous cell sources, ii) recapitulate the structure and functional properties of native skeletal muscle, which represents aligned muscle fibers interfacing within an appropriate, well-organized (ECM), iii) integrate rapidly into host tissue with associated neovascularization and innervation, and iv) support scalable and patient-specific design[2, 3].

Synthetic polymers, including polycaprolactone and poly (lactic-co-glycolic) acid, often are the engineering material of choice, largely owing to their mechanical stability, design versatility, and amenability to "additive" micro- and nano-fabrication techniques (electrospinning, patterning), where cells and materials are brought together in a stepwise fashion by adding layer upon layer. Unfortunately, upon implantation in vivo, these materials are sensed as "foreign" to cells, yielding an inflammatory-mediated, foreign-body response which is known to compromise healing and lead to poor clinical outcomes. Decellularized tissues (e.g., skeletal muscle), which are processed to maintain the complex composition, structural integrity, and architectural features of tissue extracellular matrix (ECM), also have been applied. However, these graft materials induce an inflammatory reaction as well, and their dense microstructure prevents complete recellularization and muscle recovery. Alternatively, natural polymers, such as fibrinogen, type I collagen, and Matrigel alone or in combination have been employed.

For these applications, conventional casting methods have been applied where cells are mixed with natural polymers and pipetting within molds to form cylindrical or rectangular shaped constructs with randomly organized dispersions of cells. The materials are then anchored at each end to provide passive tension, which is required to promote unidirectional cell alignment and myotube formation via cell fusion. Although it is evident that these natural polymers provide cell adhesion sites and associated bioinstructive properties, they are known to exhibit high batch-to-batch variability and are less amenable to the control of their physicochemical properties and scalable fabrication processes than synthetic polymers. Despite advancements with respect to muscle engineering, the search continues for a cost-effective and customizable muscle fabrication strategy that harnesses natural muscle formation processes (known as myogenesis) and rapid integration and neurovascular regeneration in absence of inflammation following implantation within the body.

Applications of such functional engineered muscle vary. For example, such muscle could be used to repair post-oncologic or traumatic defects, or to medialize the vocal fold in cases of paresis/paralysis. Autologous, organized, engineered muscle that has adequate bulk, integrates into host tissue, and restores tissue structure and function in absence of inflammation does not currently exist. Therefore, there is an unmet need for advanced scalable manufacturing strategies for engineered biological compositions, such as collagen and tissue compositions for tissue restoration in the presence, or in the absence of, embedded cells.

SUMMARY OF THE INVENTION

In one aspect of the disclosure, kits for tissue reconstruction comprising a polymerizable collagen solution and a syringe are provided. In an additional aspect of the disclosure, kits comprising a solid collagen construct and a mold are provided.

In yet an additional aspect of the disclosure, solid collagen constructs comprising aligned collagen fibrils and aligned cells are provided. In a still further aspect of the disclosure, solid collagen constructs prepared by the process of extruding a polymerizable collagen solution with an extruder to generate solid collagen constructs are provided.

In yet an additional aspect of the disclosure, solid collagen constructs prepared by the process of extruding a suspension of polymerizable collagen solution and cells with an extruder to generate solid collagen constructs are provided. In a further aspect of the disclosure, tissue implants comprising solid collagen constructs are provided.

In an additional aspect of the disclosure, processes for preparing solid collagen constructs are provided comprising extruding a polymerizable collagen solution with an extruder to generate solid collagen constructs are provided.

In still a further aspect of the disclosure, processes for preparing solid collagen constructs by the process comprising extruding a suspension of polymerizable collagen solution and cells with an extruder to generate solid collagen constructs wherein the solid collagen constructs are embedded with cells are provided.

In a further aspect of the disclosure, a 3D tissue-engineered muscle implant prepared from therapeutic cells, and type I collagen oligomers through extrusion, is provided.

Still other embodiments described in the following clause list are considered to be part of the invention.

In addition any of the embodiments described in the following clause list are considered to be part of the invention.

1. A solid collagen construct comprising aligned collagen fibrils and aligned cells.
2. A solid collagen construct prepared by the process of extruding a polymerizable collagen solution with an extruder to generate the solid collagen construct.
3. The solid collagen construct of clause 2, wherein the polymerizable collagen solution is a polymerizable collagen oligomer solution.
4. The solid collagen construct of clause 3, wherein the solution is extruded into a container.
5. The solid collagen of clause 4, wherein the container is at a higher temperature than the extruder.
6. The solid collagen construct of clause 5, wherein the extruder is at about 4° C. and the container is at about 37° C.
7. The solid collagen construct of clauses 2-6, wherein the extruder is a syringe.
8. The solid collagen construct of clauses 3-7, wherein the polymerizable collagen oligomer solution comprises collagen oligomer, water, an acid, one or more salts, and a base.
9. The solid collagen construct of clause 8, wherein the polymerizable collagen oligomer solution further comprises a sugar.
10. The solid collagen construct of clauses 8-9, wherein the acid is HCl and the base is NaOH.
11. The solid collagen construct of clauses 8-10, wherein the one or more salts are $KH_2PO_4$, $Na_2HPO_4$, KCl, and NaCl.
12. The solid collagen construct of clauses 9-11, wherein the sugar is glucose.
13. The solid collagen construct of clauses 2-11, wherein the concentration of the collagen in the polymerizable collagen solution is between about 0.1 mg/ml and about 40 mg/ml.
14. The solid collagen construct of clause 13, wherein the concentration of the collagen in the polymerizable collagen solution is between about 1 mg/ml and about 10 mg/ml.
15. The solid collagen construct of clause 14, wherein the concentration of the collagen in the polymerizable collagen solution is between about 2 mg/ml and about 6 mg/ml.
16. The solid collagen construct of clause 15, wherein the concentration of the collagen in the polymerizable collagen solution is between about 3 mg/ml and about 5 mg/ml.
17. The solid collagen construct of clauses 2-16, wherein the polymerizable collagen solution is extruded at a rate of between about 1 ml/minute and about 3 ml/minute.
18. The solid collagen construct of clause 16, wherein the polymerizable collagen solution is extruded at a rate of about 2 ml/minute.
19. The solid collagen construct of clauses 2-18, wherein the pH of the polymerizable collagen solution is between about 4 and about 10.
20. The solid collagen construct of clause 19, wherein the pH of the polymerizable collagen solution is between about 6 and 8.
21. The solid collagen construct of clause 20, wherein the pH of the polymerizable collagen solution is about 7.4.
22. The solid collagen construct of clauses 2-21, wherein the solid collagen is fibrillar.
23. The solid collagen construct of clauses 2-22, wherein the polymerizable collagen solution polymerizes during extrusion in the extruder.
24. The solid collagen construct of clauses 2-23, wherein the polymerizable collagen solution polymerizes after extrusion from the extruder.
25. The solid collagen construct of clauses 4-24 wherein the container is a die or mold.
26. The solid collagen construct of clause 26, wherein the container is a mold.
27. A solid collagen construct prepared by the process comprising extruding a suspension of polymerizable collagen solution and cells with an extruder to generate a solid collagen construct wherein the solid collagen construct is embedded with cells.
28. The solid collagen construct of clause 27, wherein the polymerizable collagen solution is a polymerizable collagen oligomer solution.
29. The solid collagen construct of clauses 27-28, wherein the cells are MPC cells.
30. The solid collagen construct of clauses 27-28, wherein the cells are MEE cells.
31. The solid collagen construct of clauses 27-28, wherein the cells are ASC.
32. The solid collagen construct of clauses 27-31, wherein the polymerizable collagen oligomer suspension is extruded into a container.
33. The solid collagen construct of clause 32, wherein the container is at a higher temperature than the extruder.
34. The solid collagen construct of clause 33, wherein the extruder is at about 4° C. and the container is at about 37° C.
35. The solid collagen construct of clauses 27-34, wherein the extruder is a syringe.
36. The solid collagen construct of clauses 28-35, wherein the polymerizable oligomer solution comprises collagen oligomer, water, an acid, one or more salts, and a base.
37. The solid collagen construct of clauses 36, wherein the polymerizable collagen oligomer solution further comprises a sugar.
38. The solid collagen construct of clauses 36-37, wherein the acid is HCl and the base is NaOH.

39. The solid collagen construct of clauses 36-38, wherein the one or more salts are $KH_2PO_4$, $Na_2HPO_4$, KCl, and NaCl.
40. The solid collagen construct of clauses 37-39, wherein the sugar is glucose.
41. The solid collagen construct of clauses 27-40, wherein the concentration of the collagen in the polymerizable collagen solution is between about 0.1 mg/ml and about 40 mg/ml.
42. The solid collagen construct of clause 41, wherein the concentration of the collagen in the polymerizable collagen solution is between about 1 mg/ml and about 6 mg/ml.
43. The solid collagen construct of clause 42, wherein the concentration of the collagen in the polymerizable collagen solution is between about 3 mg/ml and about 5 mg/ml.
44. The solid collagen construct of clauses 27-43, wherein the polymerizable collagen suspension is extruded at a rate of between about 1 ml/minute and about 3 ml/minute.
45. The solid collagen construct of clause 44, wherein the polymerizable collagen suspension is extruded at a rate of about 2 ml/minute.
46. The solid collagen construct of clauses 27-45, wherein the pH of the polymerizable collagen solution is between about 4 and about 10.
47. The solid collagen construct of clause 46, wherein the pH of the polymerizable collagen solution is between about 6 and 8.
48. The solid collagen construct of clause 47, wherein the pH of the polymerizable collagen solution is about 7.4.
49. The solid collagen construct of clauses 27-48, wherein the solid collagen is fibrillar.
50. The solid collagen construct of clauses 27-49, wherein the polymerizable collagen suspension polymerizes during extrusion in the extruder.
51. The solid collagen construct of clauses 27-50, wherein the polymerizable collagen suspension polymerizes after extrusion from the extruder.
52. The solid collagen construct of clauses 32-51 wherein the container is a die or mold.
53. The solid collagen construct of clause 52, wherein the container is a mold.
54. The solid collagen construct of clauses 27-53 further comprising the step of culturing the solid collagen construct.
55. The solid collagen construct of clauses 27-54, wherein the solid collagen construct is in the form of tissues with aligned architectures.
56. The solid collagen construct of clause 55, where the tissue is selected from cardiac muscle, nerve, smooth muscle, tendon, and ligament.
57. The solid collagen construct of clause 56, wherein the tissue is a muscle.
58. The solid collagen construct of clause 57, wherein the muscle is skeletal muscle, adductor muscle, cardiac muscle, or smooth muscle.
59. Tissue implants for human or veterinary use comprising the solid collagen constructs of clauses 2-58.
60. Tissue implants of clause 59 wherein the tissue is selected from cardiac muscle, nerve, smooth muscle, tendon, and ligament.
61. The tissue implants of clause 60, wherein the tissue is a muscle.
62. The tissue implants of clause 61, wherein the muscle is skeletal muscle, cardiac muscle. or smooth muscle.
63. A process of preparing solid collagen constructs comprising extruding a polymerizable collagen solution with an extruder to generate a solid collagen construct.
64. The process of clause 3, wherein the polymerizable collagen solution is a polymerizable collagen oligomer solution.
65. The process of clause 64, wherein the solution is extruded into a container.
66. The solid collagen of clause 65, wherein the container is at a higher temperature than the extruder.
67. The process of clause 66, wherein the extruder is at about 4° C. and the container is at about 37° C.
68. The process of clauses 63-67, wherein the extruder is a syringe.
69. The process of clauses 64-68, wherein the polymerizable collagen oligomer solution comprises collagen oligomer, water, an acid, one or more salts, and a base.
70. The process of clause 69, wherein the polymerizable collagen oligomer solution further comprises a sugar.
71. The process of clauses 69-70, wherein the acid is HCl and the base is NaOH.
72. The process of clauses 69-71, wherein the one or more salts are $KH_2PO_4$, $Na_2HPO_4$, KCl, and NaCl.
73. The process of clauses 70-71, wherein the sugar is glucose.
74. The process of clauses 63-71, wherein the concentration of the collagen in the polymerizable collagen solution is between about 0.1 mg/ml and about 40 mg/ml.
75. The process of clause 74, wherein the concentration of the collagen in the polymerizable collagen solution is between about 1 mg/ml and about 10 mg/ml.
76. The process of clause 75, wherein the concentration of the collagen in the polymerizable collagen solution is between about 2 mg/ml and about 6 mg/ml.
77. The process of clause 76, wherein the concentration of the collagen in the polymerizable collagen solution is between about 3 mg/ml and about 5 mg/ml.
78. The process of clauses 63-77, wherein the polymerizable collagen solution is extruded at a rate of between about 1 ml/minute and about 3 ml/minute.
79. The process of clause 77, wherein the polymerizable collagen solution is extruded at a rate of about 2 ml/minute.
80. The process of clauses 63-79, wherein the pH of the polymerizable collagen solution is between about 4 and about 10.
81. The process of clause 80, wherein the pH of the polymerizable collagen solution is between about 6 and 8.
82. The process of clause 81, wherein the pH of the polymerizable collagen solution is about 7.4.
83. The process of clauses 63-82, wherein the solid collagen is fibrillar.
84. The process of clauses 63-83, wherein the polymerizable collagen solution polymerizes during extrusion in the extruder.
85. The process of clauses 63-84, wherein the polymerizable collagen solution polymerizes after extrusion from the extruder.
86. The process of clauses 65-85 wherein the container is a die or mold.
87. The process composition of clause 86, wherein the container is a mold.
88. A process for preparing solid collagen construct comprising extruding a suspension of polymerizable collagen solution and cells with an extruder to generate a solid collagen construct wherein the solid collagen construct is embedded with cells.

89. The process of clause 88, wherein the polymerizable collagen solution is a polymerizable collagen oligomer solution.
90. The process of clauses 88-89, wherein the cells are MPC cells.
91. The process of clauses 88-89, wherein the cells are MEE cells.
92. The process of clauses 88-89, wherein the cells are ASC.
93. The process of clauses 88-92, wherein the polymerizable collagen oligomer suspension is extruded into a container.
94. The process of clause 93, wherein the container is at a higher temperature than the extruder.
95. The process of clause 94, wherein the extruder is at about 4° C. and the container is at about 37° C.
96. The process of clauses 88-95, wherein the extruder is a syringe.
97. The process of clauses 89-96, wherein the polymerizable oligomer solution comprises collagen oligomer, water, an acid, one or more salts, and a base.
98. The process of clauses 97, wherein the polymerizable collagen oligomer solution further comprises a sugar.
99. The process of clauses 97-98, wherein the acid is HCl and the base is NaOH.
100. The process of clauses 97-99, wherein the one or more salts are $KH_2PO_4$, $Na_2HPO_4$, KCl, and NaCl.
101. The process of clauses 98-100, wherein the sugar is glucose.
102. The process of clauses 88-101, wherein the concentration of the collagen in the polymerizable collagen solution is between about 1 mg/ml and about 10 mg/ml and the solid collagen construct forms fibrils.
103. The process of clause 102, wherein the concentration of the collagen in the polymerizable collagen solution is between about 2 mg/ml and about 6 mg/ml.
104. The process of clause 103, wherein the concentration of the collagen in the polymerizable collagen solution is between about 3 mg/ml and about 5 mg/ml.
105. The process of clauses 88-104, wherein the polymerizable collagen suspension is extruded at a rate of between about 1 ml/minute and about 3 ml/minute.
106. The process of clause 105, wherein the polymerizable collagen suspension is extruded at a rate of about 2 ml/minute.
107. The process of clauses 88-106, wherein the pH of the polymerizable collagen solution is between about 4 and about 10.
108. The process of clause 107, wherein the pH of the polymerizable collagen solution is between 6 and 8.
109. The process of clause 108, wherein the pH of the polymerizable collagen solution is about 7.4.
110. The process of clauses 88-109, wherein the solid collagen is fibrillar.
111. The process of clauses 88-110, wherein the polymerizable collagen suspension polymerizes during extrusion in the extruder.
112. The process of clauses 88-111, wherein the polymerizable collagen suspension polymerizes after extrusion from the extruder.
113. The solid collagen composition of clauses 93-112 wherein the container is a die or mold.
114. The solid collagen composition of clause 113, wherein the container is a mold.
115. The process of clauses 88-114, further comprising the step of culturing the solid collagen construct.
116. The process of clauses 88-115, wherein the solid collagen construct is in the form of tissues with aligned architectures.
117. The process of clause 116, where the tissue is selected from cardiac muscle, nerve, smooth muscle, tendon, and ligament.
118. The process of clause 117, wherein the tissue is a muscle.
119. The process of clause 118, wherein the muscle is skeletal muscle, cardiac muscle, or smooth muscle.
120. The solid collagen compositions of clause 41, wherein the concentration of collagen in the polymerizable collagen solution is between about 1 mg/ml and about 10 mg/ml.
121. The solid collagen composition of clauses 24 and 51, wherein polymerization occurs after extrusion from the extruder.
122. The process of clauses 85 and 112 wherein polymerization occurs after extrusion from the extruder.
123. A kit for tissue reconstruction comprising a polymerizable collagen solution or a polymerizable collagen suspension and a syringe.
124. The kit of clause 123, wherein the polymerizable collagen solution is a solution of polymerizable collagen oligomers.
125. A kit for tissue reconstruction comprising a solid collagen construct and a mold.

DETAILED DESCRIPTION

Figure 1:
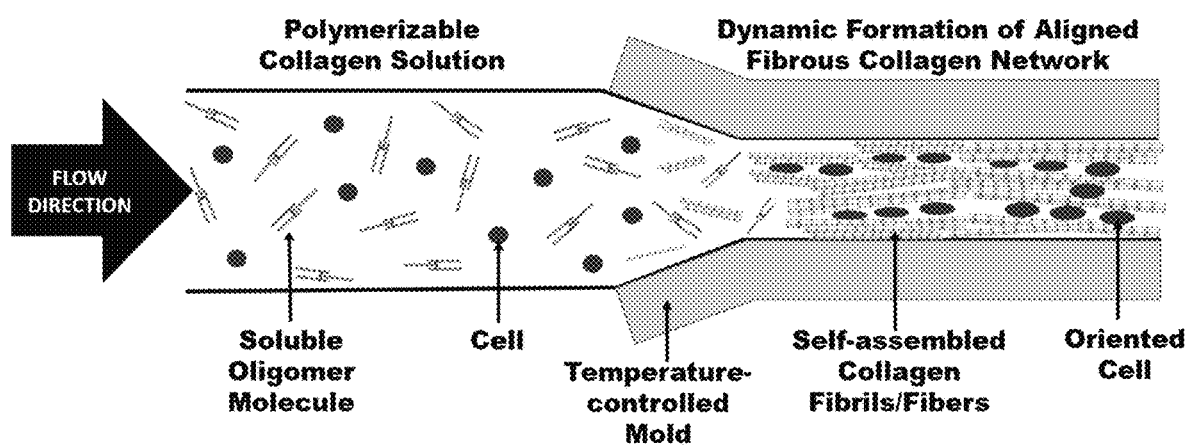
FIG. 1: Schematic showing extrusion of polymerizable type I collagen oligomer suspension containing cells through a temperature-controlled mold for rapid production of engineered tissue constructs. During extrusion the soluble oligomer molecules undergo thermally controlled polymerization to form oriented solid fibrils which further associate to form aligned composites comprised of solid fibrillar collagen and cells. Extrusion can also be done in the absence of cells.

While the concepts of the present disclosure are illustrated and described in detail in the figures and the description herein, results in the figures and their description are to be considered as exemplary and not restrictive in character; it being understood that only the illustrative embodiments are shown and described and that all changes and modifications that come within the spirit of the disclosure are desired to be protected.

Unless defined otherwise, the scientific and technology nomenclatures have the same meaning as commonly understood by a person in the ordinary skill in the art pertaining to this disclosure.

In many embodiments of the disclosure, solid collagen constructs, and processes for making them, are provided wherein the solid collagen constructs are prepared by extruding a polymerizable collagen solution with an extruder thereby generating a solid collagen construct. The polymerizable collagen solution is often a solution wherein the collagen contains oligomers such that the polymerizable collagen solution is an polymerizable solution of oligomeric collagen. In many embodiments, the collagen is only or primarily oligomeric collagen and thus contains no or substantially no monomeric collagen. The extrusion is often done into a container such as a dye or mold. Often the extrusion is done in an extruder, such as a syringe, which is kept on ice (e.g., at about 4° C.). Although the polymerizable solution may polymerize at such temperatures, the polymerization conditions are kept such that extrusion is still possible and practical. When extruded into a container such as a mold or die, the container temperature is often kept at elevated temperatures whether room temperature or body temperature (e.g., 37° C.) to accelerate polymerization.

The polymerizable solution includes or contains components such that polymerization can be initiated at 4 C and accelerated at higher temperatures. For example, a typical polymerizable collagen oligomer solution may be prepared in accordance with Example 1. In many embodiments, the polymerizable collagen oligomer solution contains collagen oligomers, such as a type 1 collagen oligomer, which has been dissolved in water and acid, such as HCl. The pH is raised in the presence of one or more salts and base, such as NaOH. A sugar may optionally be added, such as glucose. An example of a combination of salts which is the one or more salts is $KH_2PO_4$, $Na_2HPO_4$, KCl, and NaCl. For example, when a solubilized collagen oligomeric solution is acidic and is then neutralized by the one or more salts and the base such that the pH increases to the range of between about 4 and 10 including within about 6 and about 8, and further including about 7.4, polymerization spontaneously occurs with the rate of such polymerization being dependent upon temperature.

Unless explicitly defined otherwise, the term, "solid collagen construct," refers to collagen compositions made, for example, by extrusion, in accordance with the disclosure.

Some materials that may be used to practice some embodiments of the invention can be found in U.S. Pat. No. 9,878,071 B2 issued on Jan. 30, 2018 and incorporated fully herein by reference.

In some embodiments, the polymerizable collagen composition, which may be a solution or a suspension, for example may be prepared under various conditions. For example, factors such as pH, phosphate concentration, temperature, buffer composition, ionic strength, and composition and concentration of the extracellular matrix components which includes both collagen and non-collagenous molecules, may be varied by additives or changing the environmental conditions of the polymerizable collagen composition. Examples of additives include nutrients, including minerals, amino acids, sugars, peptides, proteins, vitamins (such as ascorbic acid), or glycoproteins that facilitate hematopoietic stem cell culture, such as laminin and fibronectin, hyaluronic acid, or growth factors such as platelet-derived growth factor, or transforming growth factor beta, and glucocorticoids such as dexamethasone. Other additives include fibrillogenesis inhibitors, such as glycerol, glucose, or polyhydroxylated compounds can be added prior to or during polymerization. Additional additives include cross-linking agents, such as carbodiimides, aldehydes, lysl-oxidase, N-hydroxysuccinimide esters, imidoesters, hydrazides, and maleimides, and the like can be added before, during, or after polymerization.

With regards to sourcing the collagen starting material, it may be solubilized from tissue. For example, the collagen can be prepared by utilizing acid-solubilized collagen and defined polymerization conditions that are controlled to yield three-dimensional collagen matrices with a range of controlled assembly kinetics (e.g., polymerization half-time), molecular compositions, and fibril microstructure-mechanical properties, for example, as described in U.S. patent application Ser. No. 11/435,635 (published Nov. 22, 2007, as Publication No. 2007-0269476 A1) and Ser. No. 11/903,326 (published Oct. 30, 2008, as Publication No. 2008-0268052), each incorporated herein by reference in its entirety. In other embodiments, the collagen is polymerizable collagen. In yet other embodiment, the collagen is Type I collagen.

In some embodiments, the sourced collagen starting material is unnatural collagen. As used herein, the phrase "unnatural collagen" refers to collagen that has been removed from a source tissue. Optionally, the unnatural collagen may be solubilized from the tissue source. In other embodiments, the collagen is synthetic collagen. In yet other embodiments, the collagen is recombinant collagen.

In one aspect, unnatural collagen or collagen components can be used and can be obtained from a number of sources, including for example, porcine skin, to construct the collagen compositions described herein. Suitable tissues useful as a collagen-containing source material for isolating collagen or collagen components to make the collagen compositions described herein are submucosa tissues or any other extracellular matrix-containing tissues of a warm-blooded vertebrate. Suitable methods of preparing submucosa tissues are described in U.S. Pat. Nos. 4,902,508; 5,281,422; and 5,275,826, each incorporated herein by reference. Extracellular matrix material-containing tissues other than submucosa tissue may be used to obtain collagen in accordance with the methods and compositions described herein. Methods of preparing other extracellular matrix material-derived tissues for use in obtaining purified collagen or partially purified extracellular matrix components are known to those skilled in the art. For example, see U.S. Pat. No. 5,163,955 (pericardial tissue); U.S. Pat. No. 5,554,389 (urinary bladder submucosa tissue); U.S. Pat. No. 6,099,567 (stomach submucosa tissue); U.S. Pat. No. 6,576,265 (extracellular matrix tissues generally); U.S. Pat. No. 6,793,939 (liver basement membrane tissues); and U.S. patent application publication no. US-2005-0019419-A1 (liver basement membrane tissues); and international publication no. WO 2001/45765 (extracellular matrix tissues generally), each incorporated herein by reference. In various other embodiments, the collagen-containing source material can be selected from the group consisting of placental tissue, ovarian tissue, uterine tissue, animal tail tissue, and skin tissue. In some embodiments, the collagen is selected from the group consisting of pig skin collagen, bovine collagen, and human collagen. Any suitable extracellular matrix-containing tissue can be used as a collagen-containing source material to isolate purified collagen or partially purified extracellular matrix components.

An illustrative preparation method for preparing submucosa tissues as a source of purified collagen or partially purified extracellular matrix components is described in U.S. Pat. No. 4,902,508, the disclosure of which is incorporated herein by reference. In one embodiment, a segment of vertebrate intestine, for example, preferably harvested from porcine, ovine or bovine species, but not excluding other species, is subjected to abrasion using a longitudinal wiping motion to remove cells or cell-removal is accomplished by hypotonic or hypertonic lysis. In one embodiment, the submucosa tissue is rinsed under hypotonic conditions, such as with water or with saline under hypotonic conditions and is optionally sterilized. In another illustrative embodiment, such compositions can be prepared by mechanically removing the luminal portion of the tunica mucosa and the external muscle layers and/or lysing resident cells with hypotonic or hypertonic washes, such as with water or saline. In these embodiments, the submucosa tissue can be stored in a hydrated or dehydrated state prior to isolation of the purified collagen or partially purified extracellular matrix components. In various aspects, the submucosa tissue can comprise any delamination embodiment, including the tunica submucosa delaminated from both the tunica muscularis and at least the luminal portion of the tunica mucosa of a warm-blooded vertebrate.

In some embodiments, the collagen is oligomeric collagen. The presence of oligomeric collagen enhances the self-assembly potential by increasing the assembly rate and by yielding collagen compositions with distinct fibril microstructures and increased mechanical integrity (e.g., stiffness). In some embodiments, the collagen comprises oligomeric collagen. In other embodiments, the collagen consists essentially of oligomeric collagen. In yet other embodiments, the collagen consists of oligomeric collagen.

In some embodiments, the collagen is monomeric collagen. In some embodiments, the collagen is atelocollagen. As used herein, the term "atelocollagen" refers to collagen that is treated in vitro with pepsin or another suitable protease or agent to eliminate or substantially reduce telopeptide regions which contain intermolecular cross-linking sites. In other embodiments, the monomeric collagen is telocollagen. As used herein, the term "telocollagen" refers to acid solubilized collagen that retains its telopeptide ends.

In certain embodiments, the collagen comprises oligomeric collagen and atelocollagen. In other embodiments, the collagen comprises oligomeric collagen, monomeric collagen, and atelocollagen. The amounts of oligomeric collagen, monomeric collagen, and/or atelocollagen may be formulated in the collagen compositions to advantageously maximize the stiffness, strength, fluid and mass transport, proteolytic degradation or compatibility of the engineered collagen compositions.

In any of the embodiments described herein, the collagen can have a predetermined percentage of collagen oligomers. In various embodiments, the predetermined percentage of collagen oligomers can be about 0.5% to about 100%, about 30% to about 100%, about 40% to about 100%, about 50% to about 100%, about 60% to about 100%, about 70% to about 100%, about 80% to about 100%, about 90% to about 100%, about 95% to about 100%, or about 100%. In yet another embodiment, the collagen oligomers are obtained from a collagen-containing source material enriched with collagen oligomers (e.g., pig skin).

In any of the embodiments described herein, the collagen sourced as starting material can have an oligomer content quantified by average polymer molecular weight (AMW). As described herein, modulation of AMW can affect polymerization kinetics, fibril microstructure, molecular properties, and fibril architecture of the matrices, for example, interfibril branching, pore size, and mechanical integrity (e.g., matrix stiffness). In another embodiment, the oligomer content of the purified collagen, as quantified by average polymer molecular weight, positively correlates with matrix stiffness.

In some embodiments, the collagen is reduced collagen. As used herein "reduced collagen" means collagen that is reduced in vitro to eliminate or substantially reduce reactive aldehydes. For example, collagen may be reduced in vitro by treatment of collagen with a reducing agent (e.g., sodium borohydride).

In some embodiments, the collagen is oligomer 260 collagen. As used herein "oligomer 260 collagen" is a collagen preparation made (e.g., from porcine skin), by procedures resulting in isolation of oligomers, where the collagen preparation has a prominent band at molecular weight 260, where the band is not prominent or is lacking in corresponding monomer preparations. The presence of the band can be determined by SDS polyacrylamide gel electrophoresis. Oligomer 260 collagen is further described U.S. patent application Ser. No. 13/192,276 (published Feb. 2, 2012, as Publication No. 2012-0027732 A1), incorporated herein by reference.

The solid collagen constructs herein described may be made under controlled conditions, such as by extrusion, and by changing extrusion parameters such as, for example, extrusion rate, geometry of the container (e.g., mold), viscosity of polymerizable solution or suspension, presence or absence of additives, cell density, temperature, porosity of extrusion container (e.g., mold) to obtain particular physical properties. For example, the solid collagen constructs may have desired collagen fibril density, pore size (fibril-fibril branching), elastic modulus, tensile strain, tensile stress, linear modulus, compressive modulus, loss modulus, fibril area fraction, fibril volume fraction, collagen concentration, cell seeding density, shear storage modulus (G' or elastic (solid-like) behavior), and phase angle delta (.delta. or the measure of the fluid (viscous)—to solid (elastic)—like behavior; .delta. equals 0.degree. for Hookean solid and 90.degree. for Newtonian fluid).

As used herein, a "modulus" can be an elastic or linear modulus (defined by the slope of the linear region of the stress-strain curve obtained using conventional mechanical testing protocols; i.e., stiffness), a compressive modulus, a loss modulus, or a shear storage modulus (e.g., a storage modulus). These terms are well-known to those skilled in the art.

As used herein, a "fibril volume fraction" (i.e., fibril density) is defined as the percent area of the total area occupied by fibrils in three dimensions.

In any embodiment described herein, the fibril volume fraction of the collagen composition is about 1% to about 60%. In various embodiments, the collagen composition can contain fibrils with specific characteristics, for example, a fibril volume fraction (i.e., density) of about 2% to about 60%, about 2% to about 40%, about 5% to about 60%, about 15% to about 60%, about 2% to about 30%, about 5% to about 30%, about 15% to about 30%, or about 20% to about 30%.

It may be desirable to control or identify the concentration of the collagen, such as the collagen oligomer in solution, since different concentrations may yield solid collagen constructs with different properties. Typical ranges of collagen concentrations in the polymerizable collagen solutions, such as polymerizable oligomer collagen solutions, include between about 0.1 mg/ml and about 40 mg/ml, including between about 1 mg/ml and about 10 mg/ml, including between about 2 mg/ml and about 6 mg/ml, including between about 3 mg/ml and about 5 mg/ml. The rate of extrusion through the extruder such as, for example, a syringe, may also be controlled. Exemplary rates include between about 1 ml/min and about 3 ml/min including, or example, about 2 ml/min.

When the solid construct polymerizes, whether in the syringe during extrusion, or after exiting the extruder such as in a container (such as a die or mold), or both, the solid collagen construct may be in the form of fibrils. Such fibrils may be aligned due to the extrusion process such as for example, as see in FIG. 1 and FIG. 7. Such alignment can be beneficial in the preparation of implants for tissues that have similar alignment geometries. In these and other embodiments of the invention, solid collagen constructs, and processes for preparing them, are provided by extruding a suspension comprising a polymerizable collagen solution with cells, such as a polymerizable collagen oligomer solution, with an extruder to generate a solid collagen construct wherein the solid collagen construct is embedded with cells. Example of such cells include MCC, MEE, and/or ASC cells. In such embodiments, the suspension may be extruded into a container such as a die or a mold. The temperature of the extruder may be kept on ice (e.g., at about 4° C.) and the container, such as the die or mold, at room temperature or body temperature (e.g., at about 37° C.) to accelerate polymerization. The extruder may be a syringe. The polymerizable solution contains components such that polymerization can be initiated at 4° C. and accelerated at higher temperatures. For example, a typical polymerizable collagen oligomer solution may be prepared in accordance with Example 1. In many embodiments, the polymerizable collagen oligomer solution contains collagen oligomers, such as a type 1 collagen oligomer, which has been dissolved in water and acid, such as HCl. The pH is raised in the presence of one or more salts and base, such as NaOH. A sugar may optionally be added, such as glucose. An example of a combination of salts which is the one or more salts is $KH_2PO_4$, $Na_2HPO_4$, KCl, and NaCl. For example, when a solubilized collagen oligomeric solution is acidic and is then neutralized by the one or more salts and the base such that the pH increases to the range of between about 4 and 10 including within about 6 and about 8, and further including about 7.4, polymerization spontaneously occurs with the rate of such polymerization being dependent upon temperature.

It may be desirable to control or identify the concentration of the collagen, such as the collagen oligomer in solution, since different concentrations may yield solid collagen constructs with different properties. Typical ranges of collagen concentrations in the polymerizable collagen solutions, such as polymerizable oligomer collagen solutions, include between about 0.1 mg/ml and about 40 mg/ml, including between about 1 mg/ml and about 10 mg/ml, including between about 2 mg/ml and about 6 mg/ml, including between about 3 mg/ml and about 5 mg/ml.

The rate of extrusion of the polymerizable collagen suspension through the extruder such as, for example, a syringe, may also be controlled. Exemplary rates include between about 1 ml/min and about 3 ml/min including, or example, about 2 ml/min. When the solid construct polymerizes, whether the suspension is in the syringe during extrusion, or after exiting the extruder such as in a container (such as a die or mold), or both, the solid collagen construct may be in the form of fibrils. Such fibrils may be aligned due to the extrusion process such as for example, as see in FIG. 1 and FIG. 7. Such alignment can be beneficial in the preparation of implants for tissues that have similar alignment geometries. In many embodiments, the solid collagen constructs with embedded cells may further be cultured.

The solid collagen constructs embedded with cells may be used to form tissues with aligned architectures such as muscles, nerves, tendons, or ligaments. Examples of muscle tissue include cardiac muscle, smooth muscle, skeletal muscle, and adductor muscle. Collagen constructs made with or without embedded cells may be used as implants in human or veterinary applications such as in tissues form tissues with aligned architectures such as muscles, nerves, tendons, or ligaments. Examples of muscle tissue include cardiac muscle, smooth muscle, skeletal muscle, and adductor muscle. The kits of the disclosure may contain polymerizable collagen solutions or polymerizable collagen suspension, such as from oligomeric collagen, provided that the rate of polymerization is low enough to allow for extrusion. Other kits may comprise solid collagen constructs. Such kits may be used for tissue reconstruction.

In many embodiments, the processes of the disclosure for making involves extrusion of polymerizable collagen solutions. Polymerization describes the process by which soluble collagen molecules aggregate to form solid collagen fibrils surrounded by a fluid. For example, extrusion of polymerizable collagen solutions during polymerization yields compositions where solid collagen fibrils are preferentially oriented in the direction of flow. Extrusion parameters, including temperature, oligomer concentration, flow rate, etc. can be modulated to yield different compositions. Autologous stem, progenitor, or differentiated cells and oligomer collagen for generation of different tissue compositions. For example, tissue constructs that exhibit the greatest in-vitro muscle forming activity, as measured by the extent of myoblast fusion and myotube formation, is observed with the extrusion of an appropriate high density cells cultured within a low fibril density (stiffness) matrix formed from soluble collagen oligomers. In yet another example, engineered muscle constructs can be generated by combining oligomer collagen with myoblasts cell lines, muscle progenitor cells (MPC) (for example, autologous MPCs), or motor endplate expressing MPCs (MEE). For instance, constructs fashioned from oligomers and motor endplate expressing MPCs (MEE) provide advantageous in-vivo tissue integration and muscle regeneration compared to MPC-oligomer constructs. As used herein, term "constructs" refers to solid collagen materials wither with or without embedded cells.

In other embodiments, solid collagen constructs such as aligned ASC-oligomer or fibrillar collagen constructs are formed by extrusion through a temperature-controlled mold, and applied to polymerizable oligomer solutions during polymerization in the presence of cells in the case of ASC-oligomer constructs or in the absence of cells in the case of fibrillar collagen constructs.

In other embodiments, 3D tissue-engineered muscle implant prepared from therapeutic cells, and type I collagen oligomers through extrusion, is provided. Examples of therapeutic cells including stem or progenitor cells (for example MPCs) or their derivatives (for example MEE MPCs). In these and other embodiments, 3D-Engineered muscle implants may be constructed from autologous cell sources and polymerizable collagen oligomers to avoid adverse immune and inflammatory responses. Such implants recapitulate the structure and functional properties of native skeletal muscle, and represents aligned muscle fibers interfacing within an appropriate, well-organized and persistent extracellular matrix (ECM) that shows low turnover rate or high resistance to proteolytic degradation. The biological constructs integrate rapidly into host tissue in absence of immune or inflammatory response with associated neovascularization and innervation, interfacial tissue regeneration, and support scalable and patient-specific design. The ratio of cell density and the oligomer fibril density may be optimized to achieve cell-matrix physical and biochemical associations that recreate those found between muscle cells and the endomysium in vivo, resulting in accelerated in-vitro myotube formation and in-vivo muscle regeneration. For example, such solid collagen constructs made according to the disclosure can be used for reconstructing damaged muscle and cartilaginous hemilaryngeal defects as well as other muscle defects, which may result from a number of conditions including traumatic injury, tumor extraction, muscle degeneration, myopathy, and congenital malformations.

In various embodiments of the invention, the myogenic potential of MPCs may be interfaced with polymerizable collagens to create an engineered muscle for laryngeal reconstruction in the presence or in the absence of recurrent laryngeal nerve injury. For example, a MPC-oligomer construct may be extruded to achieve a fibril density that mimics those found between muscle cells and the endomysium in vivo, resulting in accelerated in-vitro myotube formation. Additional benefit of recapitulating the muscle-ECM interface was evident from the time-dependent recovery of muscle volume and function along with regeneration of supporting cartilaginous structures following implantation in vivo. Thus, for example, the advantage of the constructs of the disclosure is that they integrate with the surrounding normal tissue and immediately induce functional muscle formation within defect sites and do not trigger an inflammation response. Conventional muscle engineering strategies, which involve synthetic and natural biomaterials, are designed to degrade slowly so that they can be replaced by host deposited tissue. However, the ability of the host to generate new muscle in this situation in limited, especially since these materials typically induce inflammation.

The constructs described herein enjoy many advantages over the prior art engineered muscle tissue including i) the use of a standardized and customizable polymerizable collagen formulations, ii) the promotion of interfacial tissue regeneration by minimizing inflammation and iii) acceleration of functional muscle restoration through rapid innervation. For example, laryngeal reconstruction represents an unmet need because the methods to date are not suitable to perform such reconstructions. These prior methods have various limitations such as the lack of new muscle formation, limited vascularization and innervation which is required for functional muscle as well as triggering inflammation which delays healing. Currently, clinical strategies result in scar formation and loss of normal structure and function. By comparison, the methods and materials of the disclosure involve engineered biological muscle, prepared from solid collagen constructs embedded with cells, overcomes these limitations.

In many embodiments, and with respect to patient-specific human laryngeal muscle, the solid collagen constructs herein feature i) alignment of component MPCs and a collagen-fibril ECM rapidly upon fabrication (for example, via extrusion methods) and ii) induction of motor endplate expression to accelerate innervation following in-vivo implantation[7]. The oligomers used within the constructs are well suited for tissue engineering and regeneration strategies since they i) exhibit rapid suprafibrillar self-assembly yielding highly interconnected collagen-fibril matrices resembling those found in vivo; ii) are standardized based upon their fibril-forming capacity; support cell encapsulation and distribution throughout the construct; and iv) allow customized multi-scale design across the broadest range of tissue architectures and physical properties.

SOME REPRESENTATIVE EXAMPLES

Example 1: Preparation of Collagen Composition

Type I collagen oligomers were derived from the dermis of closed herd pigs and prepared as described previously (Bailey J L, Critser P J, Whittington C, Kuske J L, Yoder M C, Voytik-Harbin S L; Collagen oligomers modulate physical and biological properties of three-dimensional self-assembled matrices, *Biopolymers* (2011) 95(2):77-93 and Kreger S T, Bell B J, Bailey J, Stites E, Kuske J, Waisner B, Voytik-Harbin S L; Polymerization and matrix physical properties as important design considerations for soluble collagen formulations, *Biopolymers* (2010) 93(8):690-707, both incorporated herein by reference). Prior to use, lyophilized collagen oligomers were solubilized in 0.01 N hydrochloric acid and rendered aseptic by chloroform exposure at 4° C. or sterile filtration using a 0.22 µm filter. A Sirius Red (Direct Red 80) assay was used to determine collagen concentration. Oligomer solutions were standardized based upon purity as well as polymerization capacity according to the ASTM international consensus standard F3089-14 (ASTM Standard F3089, 2014, "Standard Guide for Characterization and Standardization of Polymerizable Collagen-Based Products and Associated Collagen-Cell Interactions", ASTM International, West Conshohocken, Pa., F3089-14, www.astm.org). Polymerization capacity is defined by matrix shear storage modulus (G') as a function of oligomer concentration of the polymerization reaction. In this way, a predictive formulary can be established that relates the concentration of a polymerizable oligomer solution to specific viscoelastic properties, namely shear storage modulus, of the resultant polymerized oligomer scaffold. Polymerization is induced using single-step neutralization with a 10× self-assembly reagent (added at a ratio of 1 part to 9 parts acidic oligomer solution) prepared according to the following recipe:

2 g $KH_2PO_4$ (FW 136.09)
11.5 g $Na_2HPO_4$ (FW 141.96)
2 g KCl (FW 74.55)
10 g glucose
80 g NaCl (FW 58.44)
20 ml 5N NaOH It should be noted that the rate of polymerization is temperature dependent, increasing, for example over the range of 4° C. and 37° C.

Example 2: Viscoelastic Properties Testing

Viscoelastic properties of polymerized oligomer constructs were determined using oscillatory shear mode on an AR2000 rheometer (TA Instruments, New Castle, Del.) as previously described (Kreger et al., 2010). Samples were polymerized on the rheometer stage for 30 min followed by a shear-strain sweep from 0.1% to 4% strain at 1 Hz. The shear storage modulus (G') at 1% strain was used as a measure of scaffold mechanical integrity.

Example 3: Myoblast Cell Line and Primary MPCs

C2C12 mouse myoblasts (ATCC, Rockville, Md.) were cultured in Dulbecco's Modified Eagle Medium (DMEM; Fisher Scientific, Chicago, Ill.) supplemented with 1% penicillin, streptomycin, amphotericin B (PSF-1; HyClone, Logan, Utah), and 10% fetal bovine serum (HyClone; Logan Utah) at 37° C. and 5% carbon dioxide. Cells were cultured to 70% confluency and used in experiments at passages 5-8. Primary MPCs were generated from skeletal muscle biopsies obtained from 12-week-old male Fischer 344 rats (Envigo, Indianapolis, Ind.) as previously described[7]. In brief, fresh muscle tissue was placed in myogenic growth medium (MGM), which consisted of DMEM supplemented with 1% PSF-1, 20% fetal bovine serum, and 0.1% chick embryo extract (Accurate Chemicals, Westbury, N.Y.). Muscle was minced and digested in 0.2% collagenase type I (EMD Millipore, Temecula, Calif.) at 37° C. for 2 hours. Digested tissue was filtered through a 100 μm cell strainer and washed 3 times with MGM. Resulting muscle fibers were suspended in MGM, plated onto untreated 100 mm petri dishes (Fisher Scientific), and cultured overnight at 37° C. within a humidified environment of 5% carbon dioxide in air. The supernatant was removed the next morning and transferred to culture flasks (Corning Life Sciences, Corning, N.Y.). Resultant primary muscle progenitor cells were cultured to 70% confluency and used in experiments at passages 3 to 5.

Example 4: Conventional Casting of Tissue Constructs

Tissue constructs were prepared by conventional casting methods resulting in composites comprising randomly organized cells and collagen-fibril scaffolds. Rat primary MSCs prepared according to Example 3 were suspended at a density of 106 cells/mL in neutralized oligomer solutions (1.5 mg/mL). Neutralization was achieved using multi-step or single-step procedures and reagents as described in Example 1. Neutralized MSC-oligomer suspensions were maintained at 4° C. prior to use. The MSC-oligomer suspension was aliquoted into a 24-well plate (500 μL/well) and subsequently polymerized at 37° C. for 10 minutes. Once polymerized, constructs were cultured for 24 hours in Dulbecco's Modified Eagle Medium (DMEM) supplemented with 1% penicillin, streptomycin, amphotericin B (PSF-1; HyClone, Logan, Utah) and 10% fetal bovine serum (HyClone; Logan, Utah) at 37° C. within a humidified environment of 5% carbon dioxide in air. Tissue constructs were fixed in 3% paraformaldehyde of culture and stained with phalloidin for visualization of the actin cytoskeleton. For 3D qualitative analysis, tissue constructs were imaged using an Olympus FluoView FV-1000 confocal system adapted to an inverted microscope (IX81, Olympus Corporation, Tokyo, Japan). Confocal image stacks were processed using Imaris software and images analyzed on ImageJ for alignment using the Directionality algorithm. As shown in FIG. 3D-F, tissue constructs formed by conventional casting methods exhibited randomly organized cells and collagen fibril scaffolds.

Example 5: Preparation of Aligned Muscle Constructs by Extrusion

Figure 2:
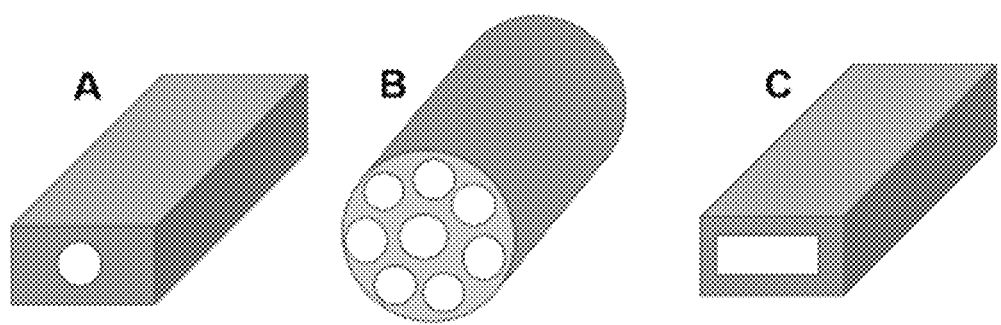
FIG. 2: Examples of extrusion mold geometries used to create engineered collagen and tissue constructs.
Figure 3:
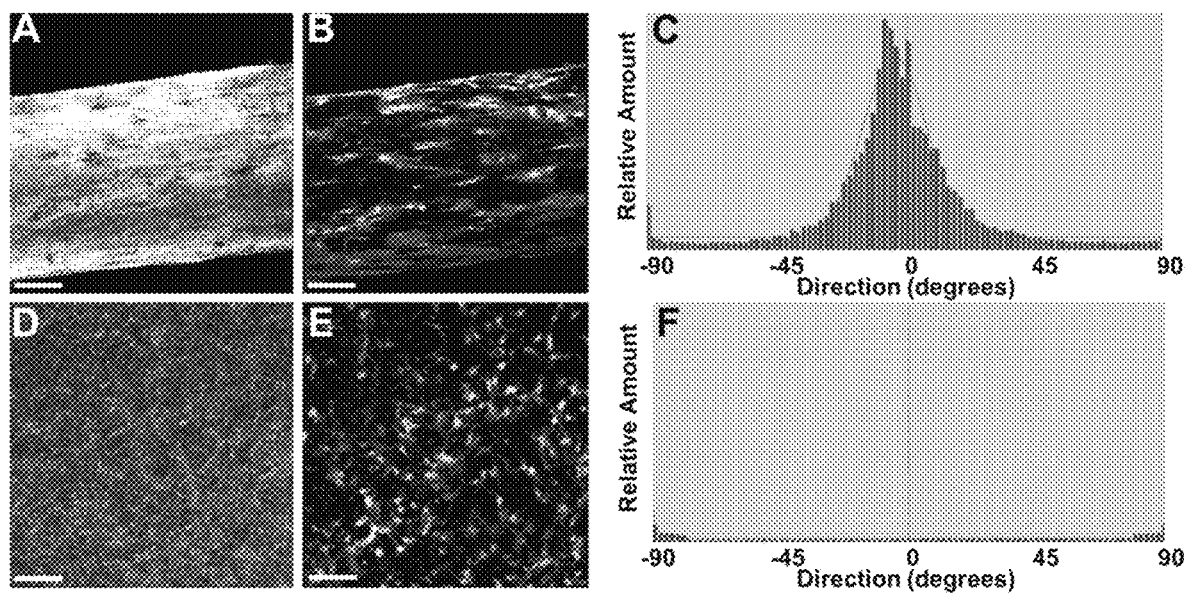
FIG. 3. Representative images and directionality analyses for engineered muscle constructs formed using extrusion method (A-C) compared to conventional casting technique (D-F). Fabricated muscle constructs were cultured 24 hours and analyzed by confocal reflection microscopy for visualization of fibril microstructure (A,D), confocal fluorescence microscopy for visualization of myoblast morphology (B,E), and ImageJ Directionality algorithm for alignment determination (C,F). Scale bar=50 μm FIG. 4A. Engineered muscle construct culture and optimization. Muscle constructs were formed by extrusion of C2C12 myoblasts at 10E6 cells/mL (a,b) or 10E7 cells/mL (c,d) suspended within type I collagen oligomer solutions prepared at 1.3 mg/mL (a,c) and 3.3 mg/mL (b,d). A. Constructs were cultured within a custom culture device for 14 days under passive tension.

Acidic oligomer solutions were prepared and standardized as described in Example 1. Neutralized oligomer solutions were prepared according to Example 2 at a final concentration of 1.5 mg/mL and maintained at 4° C. to slow polymerization rate. MPCs were then suspended in the neutralized oligomer solution at $10^7$ cells/mL and maintained at 4° C. prior to use. The 4° C. temperature was maintained by placing the solutions and suspensions on ice. The MPC-oligomer suspension (500 μL) was drawn up into a syringe and then extruded (FIG. 1) from the syringe (3 cc) at a rate of 2 mL/min into an 4-mm diameter cylinder mold prepared from Ultem (FIG. 2A and open on both ends), which was maintained at 37° C. and stayed in the mold for about 10 minutes to form "constructs". Afterwards, the constructs were transferred to a customized culture chamber and secured in tension with fasteners (FIG. 4A) and cultured in DMEM supplemented with 10% fetal bovine serum and 1% PSF-1 at 37° C. in 5% carbon dioxide in air. After 24 hours, constructs were stained with phalloidin (actin) and Draq5 (nuclei) and analyzed by confocal microscopy to visualize solid collagen-fibril scaffold and cells within the constructs. Confocal image stacks were analyzed on ImageJ for alignment using the Directionality algorithm. As indicated in FIG. 3, solid collagen fibrils (FIG. 3A) and cells (FIG. 3B) were highly aligned parallel (FIG. 3C) to the direction of flow. By contrast, constructs prepared by conventional casting methods (Example 4) exhibited random organization (FIG. 3F) of solid collagen fibrils (FIG. 3D) and cells (FIG. 3E).

Figure 4:
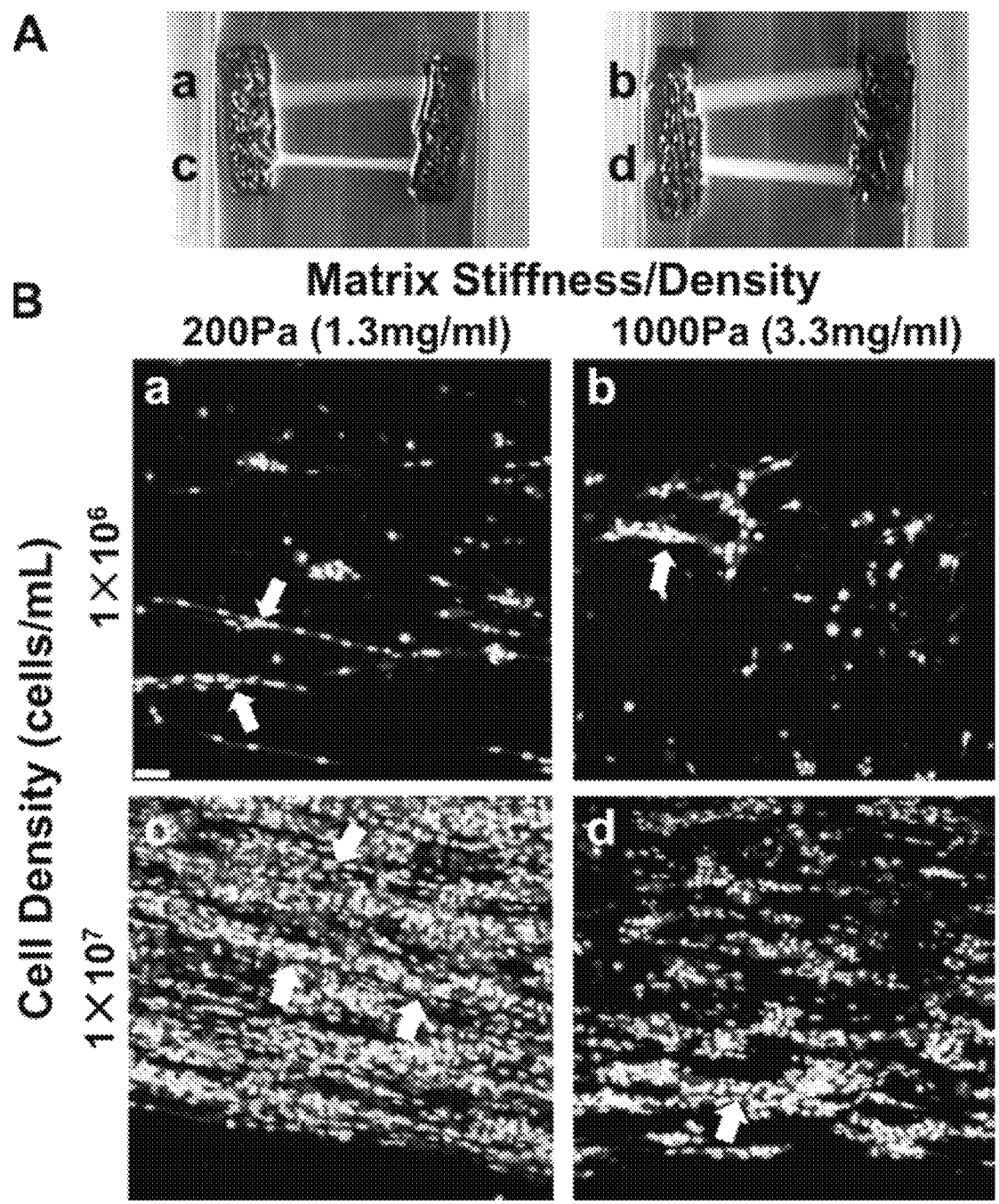
FIG. 4B. Confocal images (100 μm thickness) of 14-day constructs stained with phalloidin (F-actin) and Draq5 (nucleus) show more extensive myotube formation (white arrows) for constructs prepared at high cell densities (10E7 cells/mL) and low oligomer concentrations (1.3 mg/mL). Scale bar=50 μm FIG. 5. Engineered muscle constructs (14 days) formed by extrusion of F344 rat primary MPCs (10E7 cells/mL) suspended within type I collagen oligomer solutions prepared at 1.3 mg/mL. A. Confocal images (50 μm thickness) of 14-day constructs stained with phalloidin (F-actin) and Draq5 (nucleus) show highly aligned cell morphology and fused myotube formation. Cells were distributed throughout the entire construct volume as indicated by H&E staining of longitudinal (B) and transverse (C) sections. Scale bars=30 μm (A), 500 μm (B-C)
Figure 5:
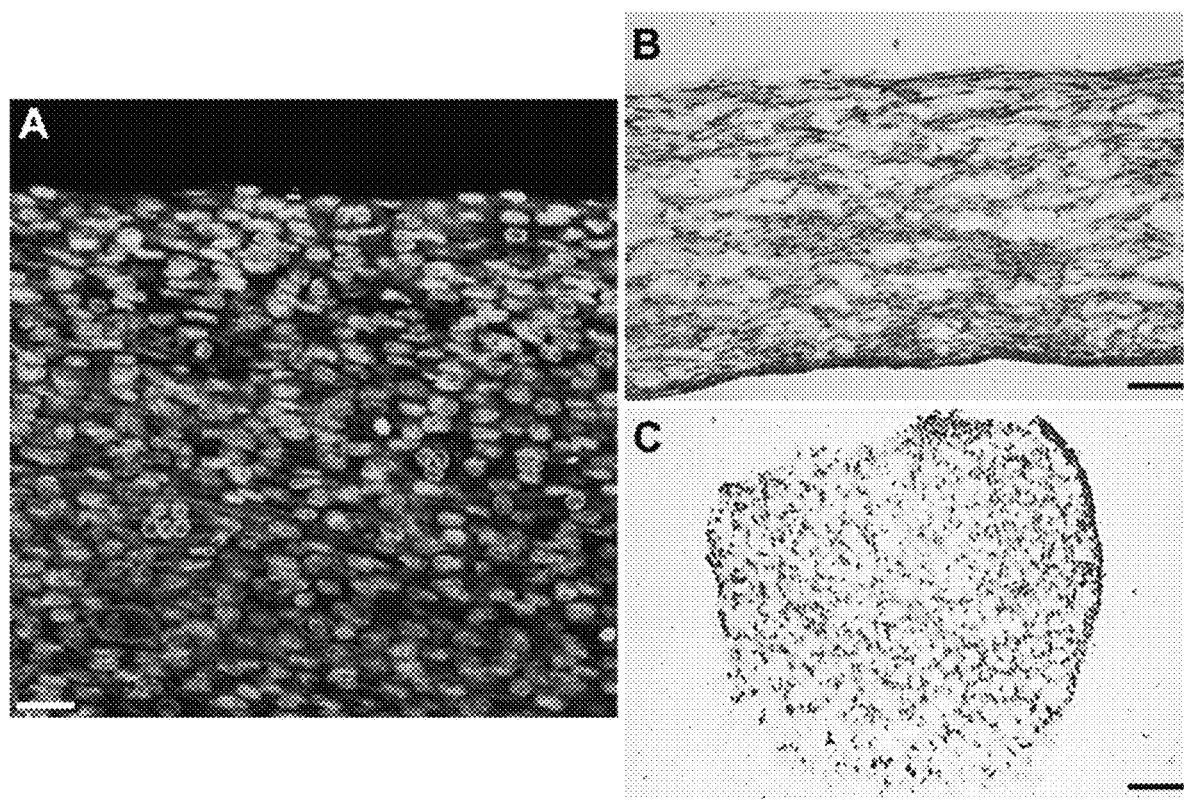

Example 6: Effect of Cell Density and Oligomer Concentration on Engineered Muscle Constructs Prepared by Extrusion The same extrusion process described in Example 5 was applied for C2C12 myoblasts at densities of $10^6$ and $10^7$ cells/mL as set forth in this Example 6. C2C12 myoblasts were suspended at each density in neutralized oligomer solutions (Example 1) prepared at either 1.3 mg/mL or 3.3 mg/mL. Following extrusion, constructs were cultured within the custom culture device for 14 days under passive tension (FIG. 4A) prior to fixation and staining with phalloidin and Draq5 for visualization of cellular actin and nuclei, respectively. As indicated in FIG. 4, constructs prepared at high cell density and low oligomer concentration (Panel c of FIG. 4B) exhibited the necessary cell-cell interactions and collagen-fibril scaffold support to facilitate a high level of cell fusion, nuclear alignment, and myotube formation. By contrast, constructs prepared at low cell density and high oligomer concentration (Panel b of FIG. 4B) exhibited the least amount of cell fusion and alignment largely owing to the increased solution viscosity and density of solid fibrils formed during polymerization. Follow-up verification studies revealed that this fabrication strategy was also applicable to primary rat MPCs, yielding highly reproducible engineered muscle with viable cells distributed throughout the construct after 2 weeks of culture (FIG. 5).

Example 7: Generation of Aligned Muscle Construct with Motor Endplate Expressing MPCs (MEE)

The same extrusion process outlined in Example 6 was applied to create aligned muscle constructs where the MPCs were induced to express motor endplates. Briefly, following extrusion constructs were cultured for 5 days after which time motor endplate expression was induced by adding acetylcholine chloride (40 nM; Tocris Bioscience, Bristol, England), agrin (10 nM; R&D Systems, Minneapolis, Minn.), and neuregulin (2 nM; R&D Systems) to the culture medium. Constructs were cultured an additional 7 days with medium changes every 3 days. Motor endplate expression was confirmed by immunostaining with ALEXA FLUOR® 594 conjugated a-bungarotoxin (Molecular Probes, Eugene, Oreg.).

Figure 6:
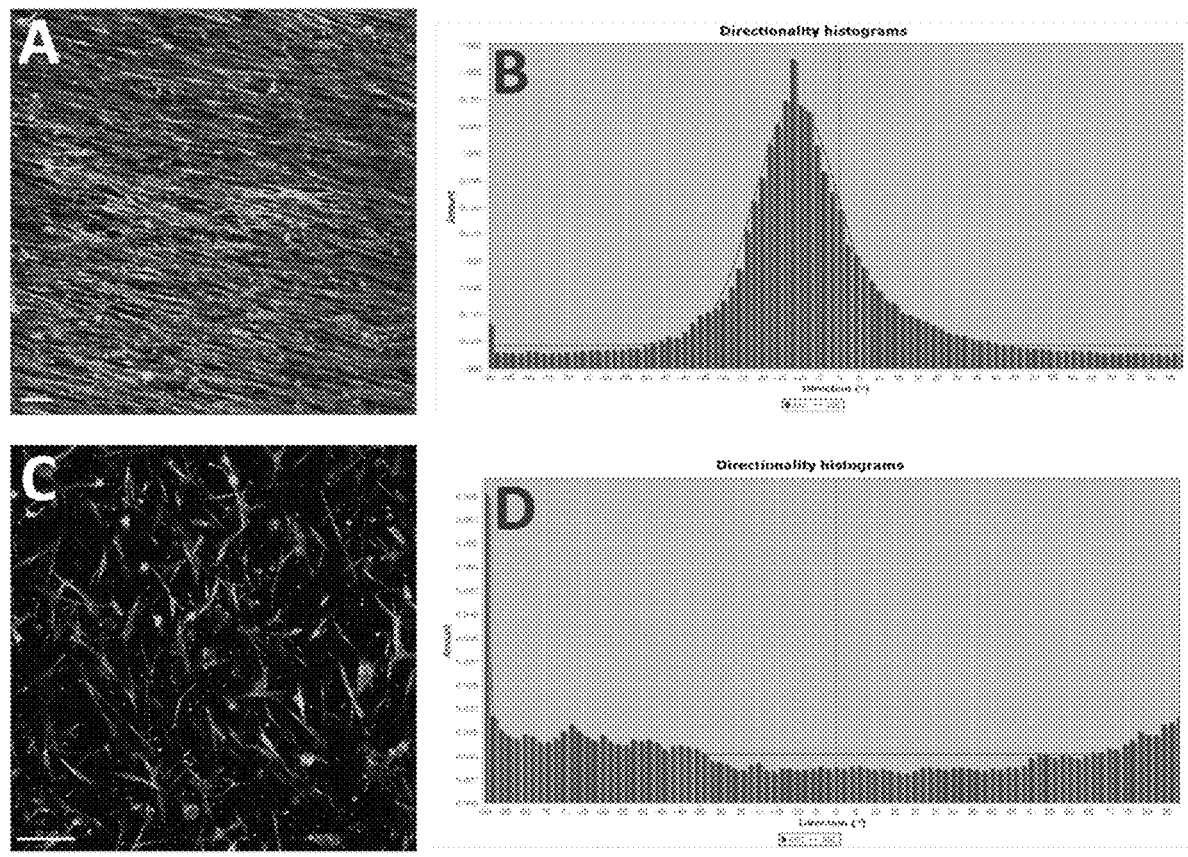
FIG. 6: Representative images and directionality analyses for engineered tissue constructs formed with adipose-derived stem cells (ASCs) suspended in type I collagen oligomer solution using extrusion method (A-B) compared to conventional casting technique (C-D). Fabricated constructs were cultured 24 hours, stained with phalloidin (F-actin) and Draq5 (nucleus) and analyzed by confocal fluorescence microscopy for visualization of cell morphology (A,C) and ImageJ Directionality algorithm for alignment determination (B,D). Scale bars=100 μm.

Example 8: Aligned Tissue Constructs Prepared by Extrusion of Human Adipose-Derived Stem Cells (ASCs) Suspended in Polymerizable Oligomer Solutions The same extrusion process described in Example 5 was applied to human adipose-derived stem cells (ASCs). ASCs represent an attractive autologous cell type for tissue engineering and regenerative medicine applications since they can be easily harvested from subcutaneous fat via conventional liposuction techniques. ASCs represent a mesenchymal stem cell source with self-renewal property and multipotential differentiation. Said differently, these cells are exhibit a high proliferative capacity and the ability to differentiate into multiple different cell types, including adipocytes, osteoblasts, tenocytes, myocytes, and neurocytes. Low passage human ASCs (Lonza) were cultured within collagen oligomer-coated flasks and maintained in complete medium comprising EGM-2 supplemented with 12% Hyclone FBS. Prior to extrusion, ASCs were suspended at a density of 500,000 cell/mL in neutralized oligomer solution (1.5 mg/mL). For comparison purposes, randomly organized oligomer-ASC constructs were prepared within standard 96-well plate using conventional casting methods as described in Example 4. Following culture for 24 hours, constructs were fixed in paraformaldehyde, stained with phalloidin (F-actin) followed by Draq5 (nuclear) for 30 minutes at room temperature, and imaged using confocal microscopy. Confocal image stacks were processed using Imaris software and images analyzed on ImageJ for alignment using the Directionality algorithm. As shown in FIG. 6A-B, tissue constructs prepared by extrusion showed uniform alignment of cells in parallel with the direction of flow. By contrast, tissue constructs prepared by conventional casting techniques exhibited randomly organized cells with no preferred directionality (FIG. 6C-D). Such randomly organized cells fail to recapitulate the structure and functional properties of native skeletal muscle.

Example 9: Creation of Aligned Collagen-Fibril Construct Via Extrusion

Figure 7:
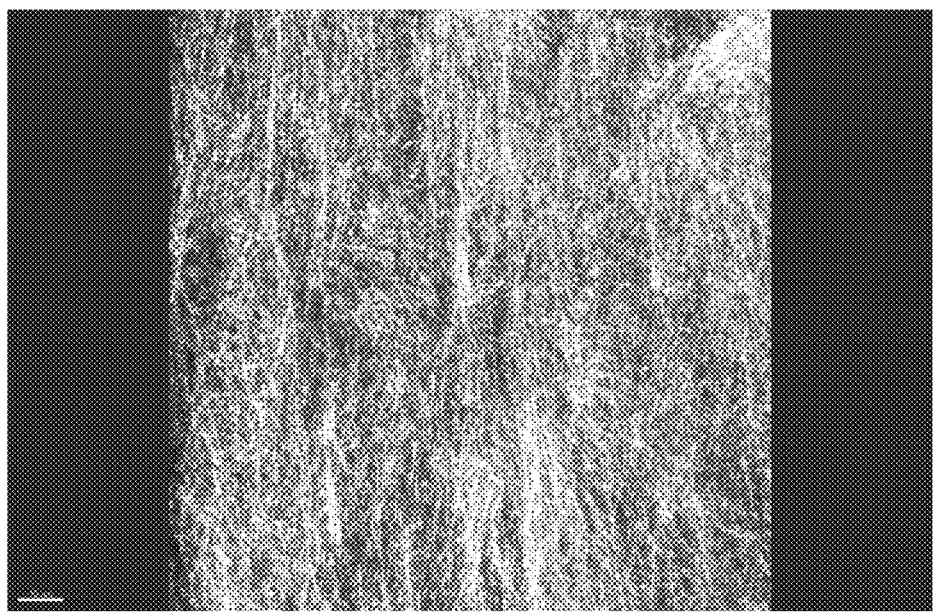
FIG. 7: Representative confocal reflection microscopy image of engineered collagen construct with aligned collagen fibrils formed by extrusion of a type I collagen oligomer solution prepared at a concentration of 3.3 mg/mL. Scale bar=10 μm.

The same extrusion process described in Example 5 was applied to oligomer solutions in absence of cells as set forth in this Example 9. Stock oligomer solution was diluted with 0.01N hydrochloric acid and neutralized as described in Example 1 to achieve a neutralized oligomer solution at a concentration of 3.3 mg/ml. The neutralized oligomer solution was kept on ice (4° C.) prior to induction of polymerization. Oligomer solution (500 µL) was extruded from a syringe (3 cc) at a rate of 2.1 mL/min into an Ultem 4-mm diameter cylinder mold, which was maintained at 37° C. Following extrusion, the construct was imaged via confocal reflection microscopy for visualization of the solid fibril architecture. As shown in FIG. 7, the resultant fibrillar collagen scaffold was highly aligned.

Example 10: Laryngectomy and Implantation of Engineered Muscle

Engineered muscle constructs formed by extrusion of primary rat MPCs suspended within neutralized oligomer solutions were evaluated in an established rat partial laryngectomy model. Neutralized oligomer solutions were prepared as described in Example 1 at a final concentration of 1.3 mg/mL. Primary rat MPCs were generated according to Example 3 and suspended in the neutralized oligomer solution at a density of 10E7 cells/mL. The suspension was extruded to form MPC-oligomer constructs as described in Example 6. Constructs were cultured for 5 days with medium changes every 2 days. On day 5, medium was changed to differentiation medium, representing DMEM supplemented with 8% horse serum (HyClone) and 1% PSF-1. Constructs were cultured for an additional 7 days to induce myotube formation. MEE-oligomer constructs were extruded as described above and cultured as described in Example 7. Oligomer only constructs were prepared by extrusion of neutralized oligomer solutions (1.3 mg/mL) in absence of cells.

The animal study protocol was approved by Purdue Animal Care and Use Committee, and institutional guidelines, in accordance with the National Institutes of Health guidelines, were followed for the handling and care of the animals. 12 Fisher 344 rats were anesthetized with intraperitoneal injection of xylazine and ketamine and then maintained on 1-4% isoflurane. The ventral larynx was exposed via a midline incision. The sternohyoid muscle was incised and reflected to expose the thyroid cartilage. A section (approximately 2 mm×2 mm) of thyroid cartilage and associated adductor muscle was removed from the left side. Animals were randomized into the following experimental groups: MPC-oligomer construct (n=4), MEE-oligomer construct (n=4), oligomer construct only (n=2), and defect only control (n=2). The sternohyoid muscle was reapposed and sutured, and subcutaneous tissue and skin closed with 5-0 Vicryl suture.

Example 11: Laryngectomy in the Presence and Absence of Recurrent Laryngeal Nerve Injury and Implantation of Engineered Muscle and Cartilage Engineered cartilage and muscle constructs were implanted in an established rat partial laryngectomy model in the presence and absence of recurrent laryngeal nerve injury. Engineered muscle constructs were formed by extrusion of primary rat MPCs suspended within neutralized oligomer solutions. Neutralized oligomer solutions were prepared as described in Example 1 at a final concentration of 1.3 mg/mL. Primary rat MPCs were generated according to Example 3 and suspended in the neutralized oligomer solution at a density of 10E7 cells/mL. The suspension was extruded to form MPC-oligomer constructs as described in Example 6. Constructs were cultured for 5 days with medium changes every 2 days. On day 5, medium was changed to differentiation medium, representing DMEM supplemented with 8% horse serum (HyClone) and 1% PSF-1. Constructs were cultured for an additional 7 days to induce myotube formation. MEE-oligomer constructs were extruded as described above and cultured as described in Example 7.

The animal study protocol was approved by Purdue Animal Care and Use Committee, and institutional guidelines, in accordance with the National Institutes of Health, were followed for the handling and care of the animals. Fisher 344 rats were anesthetized with intraperitoneal injection of xylazine and ketamine and then maintained on 1-4% isoflurane. The ventral larynx was exposed via a midline incision. The sternohyoid muscle was incised and reflected to expose the thyroid cartilage. A section (approximately 2 mm×2 mm) of thyroid cartilage and associated adductor muscle was removed from the left side. Animals were randomized into groups receiving engineered constructs with MPC or MEE cells with and without RLN injury. All groups received identical engineered cartilage implants with endpoints at 1, 3, and 6 months. The muscle construct was placed into the defect (similar to a medialization laryngoplasty implant), followed by the cartilage construct over top with extrusion prevented by suturing overlying sternohyoid muscles over the cartilaginous defect. For groups with RLN injury, the left recurrent laryngeal nerve was cauterized as it entered the larynx. The subcutaneous tissue and skin were then closed with 5-0 Vicryl suture.

Example 12: Video Laryngoscopy and Laryngeal Electomyography (EMG)

Video laryngoscopy and/or laryngeal electromyography were performed on anesthetized rats at 1, 3, and 6 month timepoints following partial laryngectomy and reconstruction as described in Examples 10 and 11. Video laryngoscopy was performed using a rigid endoscope with attached camera. Electromyogram (Niking Viking Quest electromyography machine, Madison, Wis.) was used with a 25-gauge bipolar concentric needle, settings with amplitude of 50 to 100 µV, 10- to 100-ms sweep speeds, and a grounding clamp at the exposed lateral sternocleidomastoid muscle. The EMG recording needle was inserted directly into the center of the defect/implant site, the adductor (TA) muscle complex, and the posterior cricoarytenoid (PCA) muscle during laryngospasm and at rest. Immediately following laryngoscopy and electromyography procedures, rats were humanely euthanized and tissue collected.

Example 13: Histopathological and Histochemistry Assessment

Histopathological analysis was performed at 1, 3, or 6 month timepoints following partial laryngectomy and reconstruction as described in Examples 10 and 11. After euthanasia, rat larynges and associated implants were harvested en bloc, fixed in 4% paraformaldehyde overnight, and then transferred to 30% sucrose at 4° C. for an additional 24 hours. Cryosections (25 µm thickness) were prepared on a THERMO SCIENTIFIC® CRYOTOME® (Fisher Scientific, Kalamazoo, Mich.). Sections were stained with hematoxylin & eosin (H&E) and Alcian blue for histopathological analysis. Slides were viewed on a Nikon upright microscope (Eclipse E200, Nikon, Melville, N.Y.) and images captured with a Leica camera (DFC480, Leica Buffalo Groove, Ill.). Myofiber diameter was measured using Image J software (NIH).

For histochemistry analysis, all specimens were washed with phosphate buffered saline (PBS) 3 times, permeabilized with 0.1% Triton X-100 for 20 minutes, and blocked with 1% BSA for 2 hours. Whole engineered muscle constructs were incubated overnight at 4° C. with ALEXA FLUOR® 488 conjugated phalloidin (1:25 Molecular Probes, Eugene, Oreg.) for visualization of F-actin and counterstained with Draq5 (1:1000 Cell Signaling, Danvers, Mass. 4084L) nuclear stain. For staining tissue explant cryosections, beta III tubulin conjugated primary antibody (1:10 NL647 Molecular Probes) was applied and incubated overnight at 4° C. After rinsing extensively, slides were incubated with ALEXA FLUOR® 594 conjugated a-bungarotoxin (1:100) for 2 hours at room temperature. Slides were rinsed and mounted with Fluorogel for imaging on an Olympus Fluoview confocal microscope (IX81, Olympus Waltham, Mass.) or Zeiss LSM 880 confocal microscope (Oberkochen, Germany).

Figure 8:
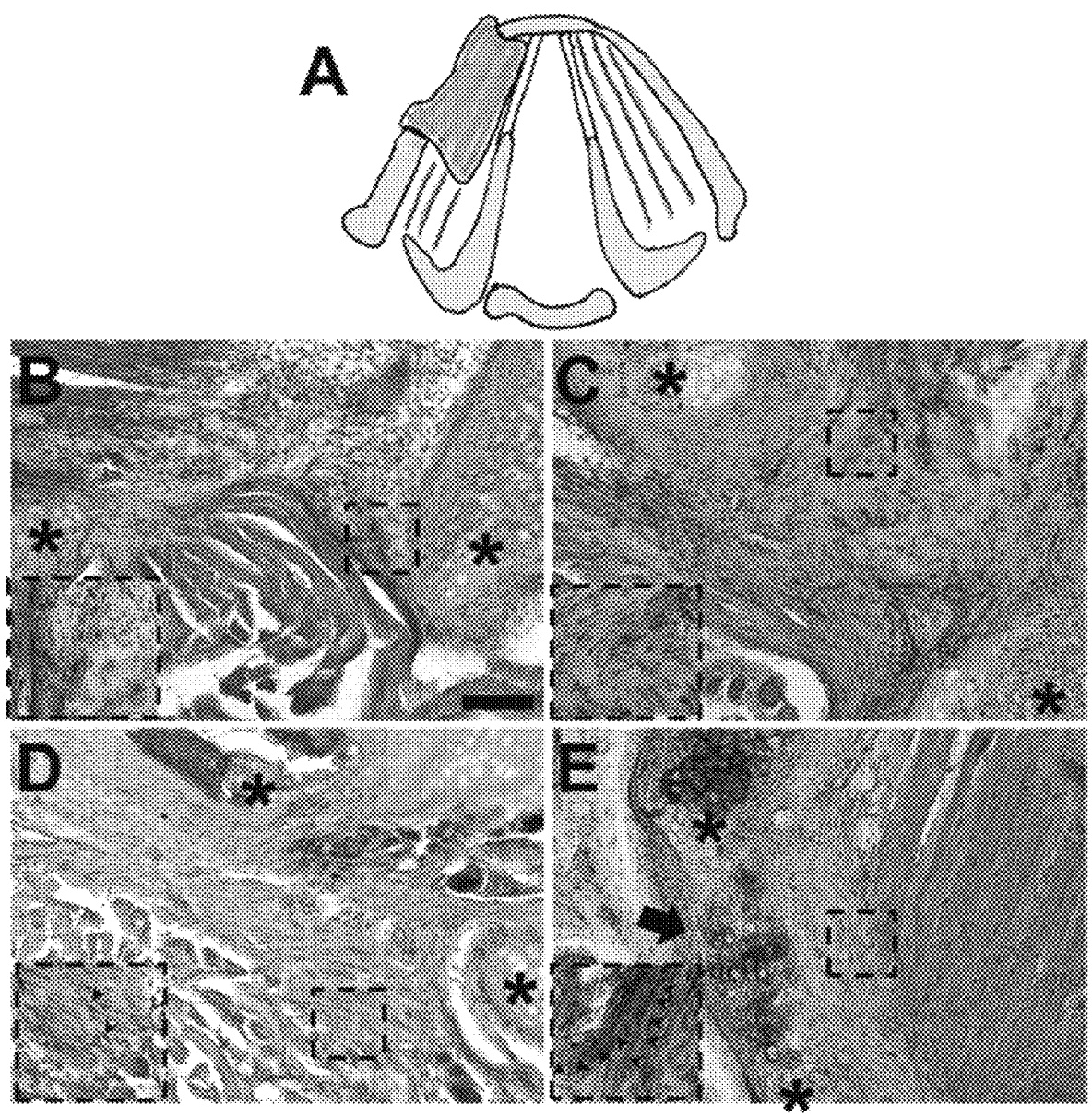
FIG. 8. (A) Schematic showing partial laryngectomy model, which involved removal of a section of hemi-thyroid cartilage and associated adductor muscle from left side. Cross-section of rat larynx showing surgical procedure and implant placement. (B-E) Representative H&E stained sections of untreated control defect (B, 2 months) and defects treated with oligomer-only implant (C, 2 months), engineered muscle implant (D, 1 month), and engineered muscle implant (E, 3 months). Untreated defect (B) showed gap filled with native sternohyoid muscle and healing via inflammation and fibrotic scar tissue formation. Oligomer-only group showed no significant inflammatory response and construct populated with mesenchymal cells. Engineered muscle implants showed progressive increase in volume of striated muscle (boxed areas and inserts; inserts represent high magnification of boxed areas) and cartilage regeneration (arrow) over time with similar responses observed for both MPC- and MEE-oligomer implants). Asterix (*) indicate edges of cartilage defect. Scale bar=200 μm FIG. 9. Representative electromyography (EMG) tracings captured at 50 μV amplitude and 10 ms sweep speeds during active laryngospasm to detect firing within engineered muscle implant 3 months following implantation (A,B) or native adductor muscle complex (C). A. Defect treated with engineered muscle prepared with MPCs (MPC Muscle) generated abundant, variable-sized motor unit potentials. B. Engineered muscle prepared with motor endplate expressing MPCs (MEE Muscle) generated potentials that were significantly larger in amplitude and frequency compared to MPC Muscle and native adductor muscle. C. Native adductor muscle complex demonstrated bursts of motor unit potentials during laryngospasm.
Figure 9:
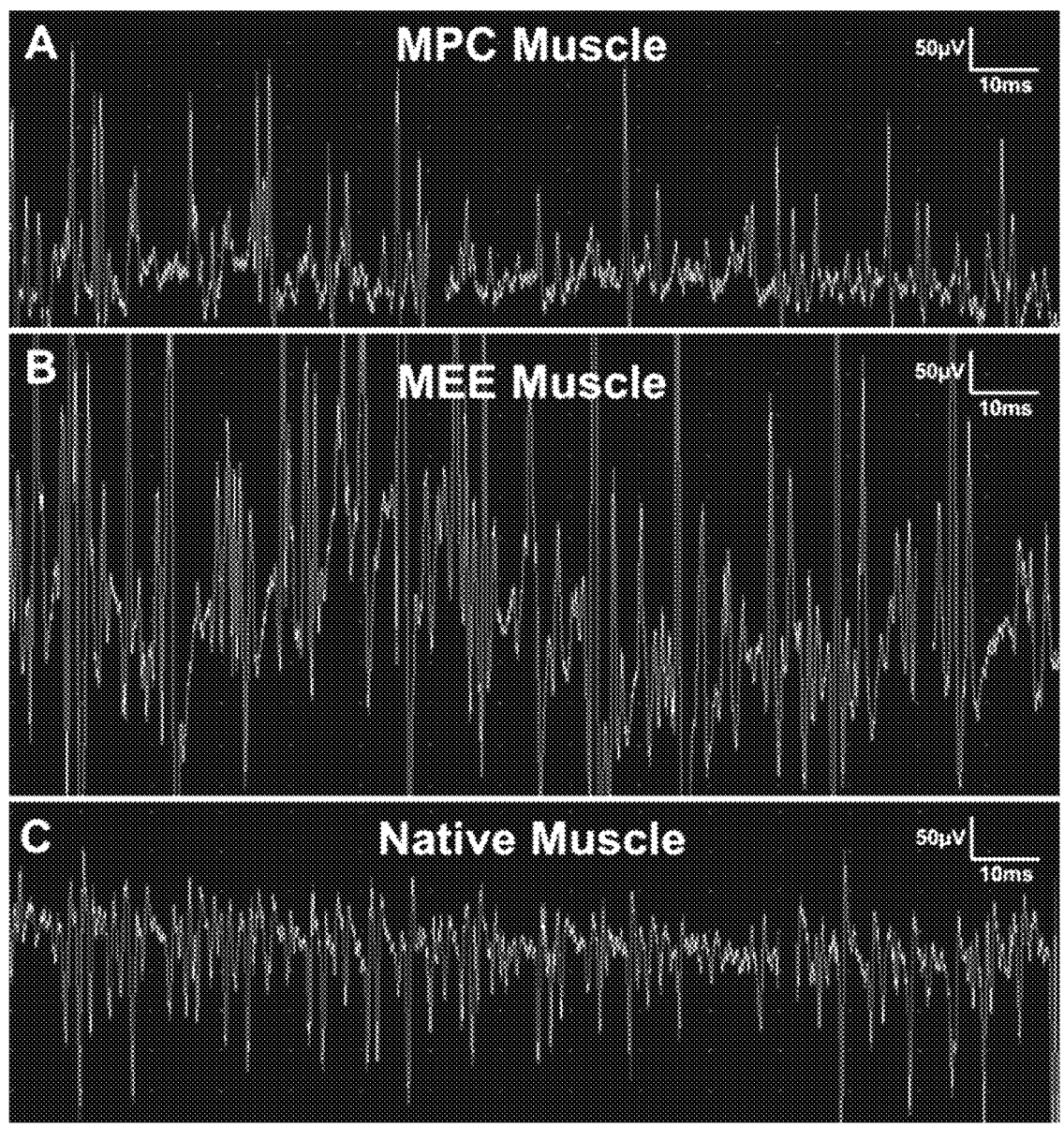
Figure 10:
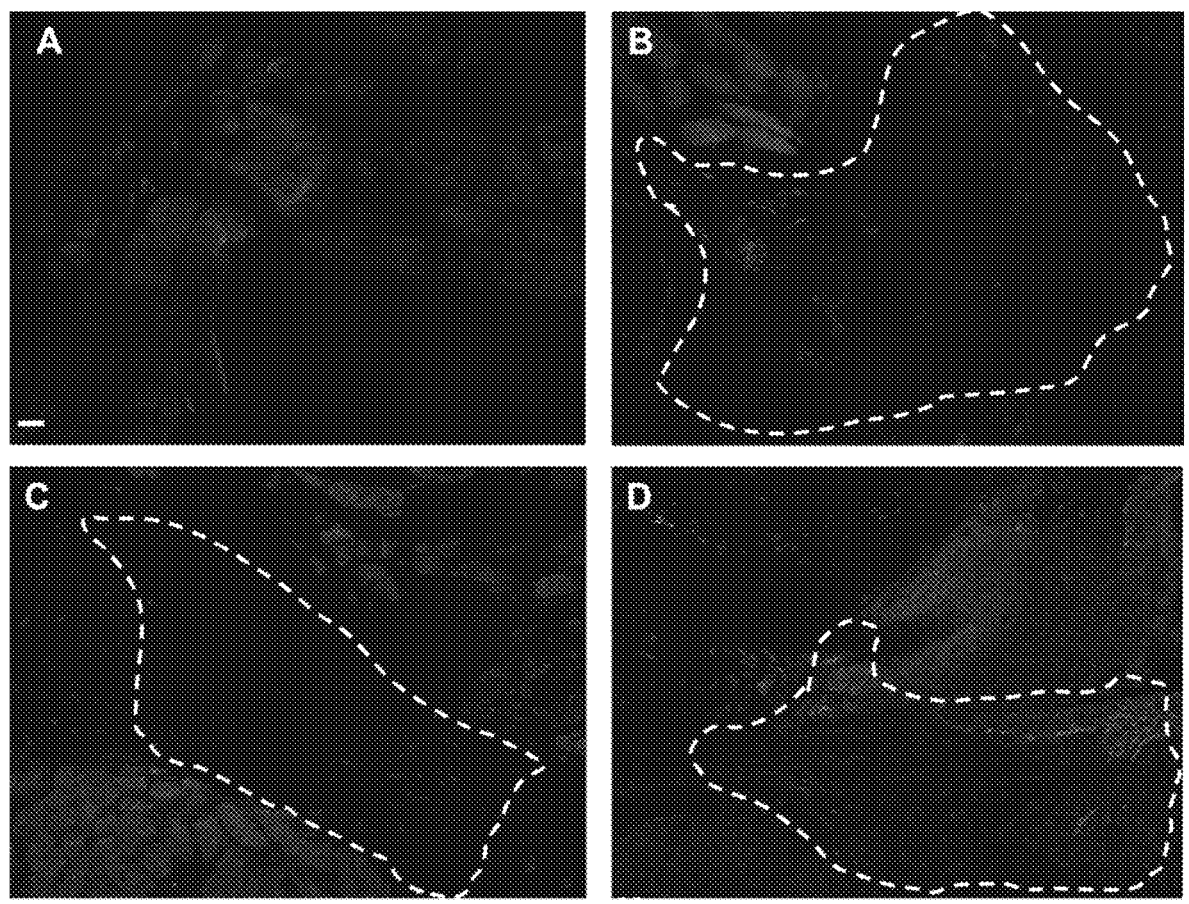
FIG. 10. Anti-beta III tubulin and α-bungarotoxin staining of (A) untreated control defect, (B) oligomer-only control, (C) MSC-oligomer construct, and (D) MEE-oligomer construct at 3 months following surgical implantation post-op. Dotted line outlines approximate construct boundaries. The MEE-oligomer construct (D) showed increased innervation when compared to the MEE-oligomer construct (C). Both the MEE- and MSC-oligomer constructs exhibited increased innervation when compared to the oligomer-only and untreated controls. Scale bar=100 μm

Example 14: Reconstruction of Laryngeal Defects with MPC-Oligomer Constructs Yields Myogenesis, Neurovascular Regeneration, and Tissue Integration in Absence of an Inflammatory-Mediated Foreign Body Response Laryngectomy and implantation of engineered muscle was performed as described in Example 10. During the post-surgical period, all animals steadily gained weight and showed no signs of laryngeal compromise. As expected, partial laryngectomy with resection of cartilage and muscle and no treatment resulted in a healing response marked by inflammation and fibrous tissue formation (scar tissue) within the defect area (FIG. 8B). In contrast, oligomer implants, with and without MPCs, integrated rapidly with adjacent host tissues, showing no significant inflammatory reaction or proteolytic degradation (FIG. 8B-E). A surprising finding was that chondrogenesis accompanied muscle regeneration over time (FIG. 8E). Compared to the oligomer only group, MPC-oligomer and MEE-oligomer constructs showed more rapid muscle regeneration and maturation as evidenced by obvious striations within the implants as early as 1 month that became more evident at 3 months. By 3 months, the relative extent of striated muscle increased, and was supported by neurogenesis, as evidenced by prominent beta III tubulin staining arising from the graft-host tissue interface (FIG. 10). Interestingly, results based on beta III tubulin and α-bungarotoxin staining indicated that the greatest level of innervation was achieved with the MEE-oligomer group. Qualitative EMG measurements provided further corroborating evidence of enhanced innervation of the MEE-oligomer constructs, with the MEE-oligomer group demonstrating the greatest level of motor unit activity (recruitment) during laryngospasm (FIG. 9).

Results of these studies suggest that aligned MEE-oligomer constructs contributed to rapid tissue integration and regeneration in the absence of any significant inflammatory reaction or rapid proteolytic degradation, yielding restored muscle with enhanced innervation on histology, and functional elicitation of motor unit potentials. Major advantages of the model include the use of autologous cells, aligned muscle constructs for rapid restoration of vascularization, innervation, and function, and a scalable fabrication method that can be translated into patient-specific designs.

Figure 11:
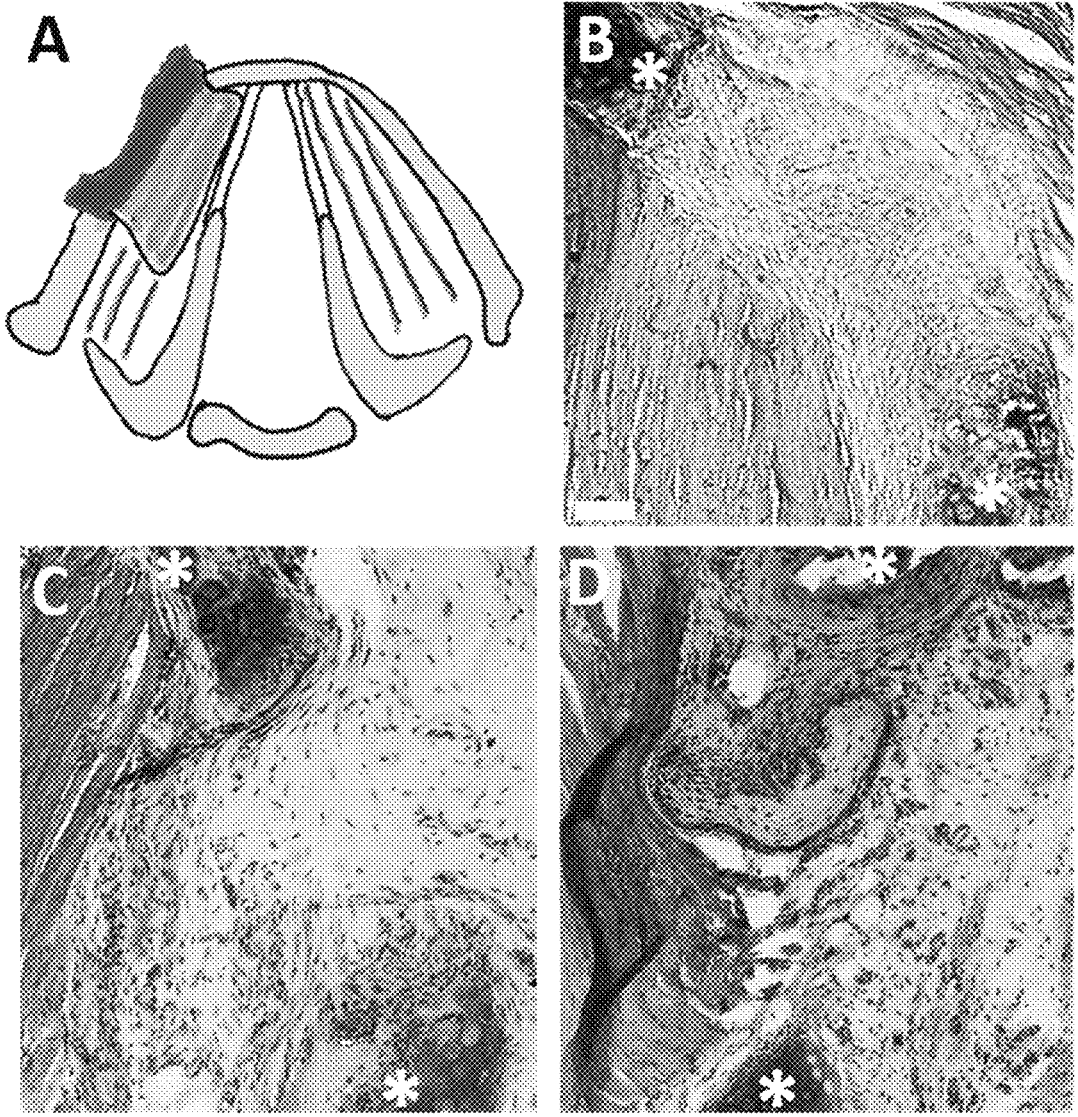
FIG. 11: (A) Schematic showing partial laryngectomy model, which involved removal of a section of hemi-thyroid cartilage and associated underlying adductor muscle in the presence or absence of recurrent laryngeal nerve injury. Cross-section of rat larynx showing surgical reconstruction with tissue-engineered cartilage and muscle implants. The cartilage constructs showed progressive remodeling, increased proteoglycan deposition, and maturation over the 1, 3, and 6 month timepoints (B, C, D respectively). Asterix represents edges of surgically created defect. Scale Bar=100 μm
Figure 12:
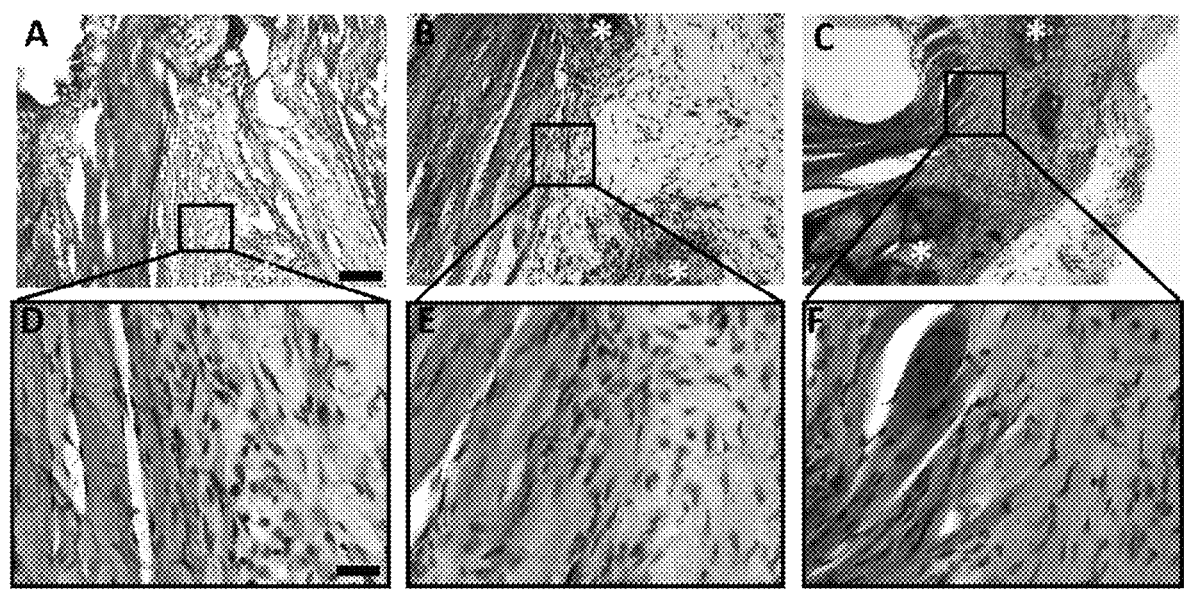
FIG. 12: H&E staining shows progressive restoration of partial laryngectomy defect reconstructed with engineered muscle constructs at 1 month (A,D), 3 months (B,E), and 6 months (C,F), marked by muscular integration, regeneration, and maturation with no inflammatory response. Asterix marks edges of surgical defect. Scale Bar: A-C 100 μm; D-F 25 μm
Figure 13:
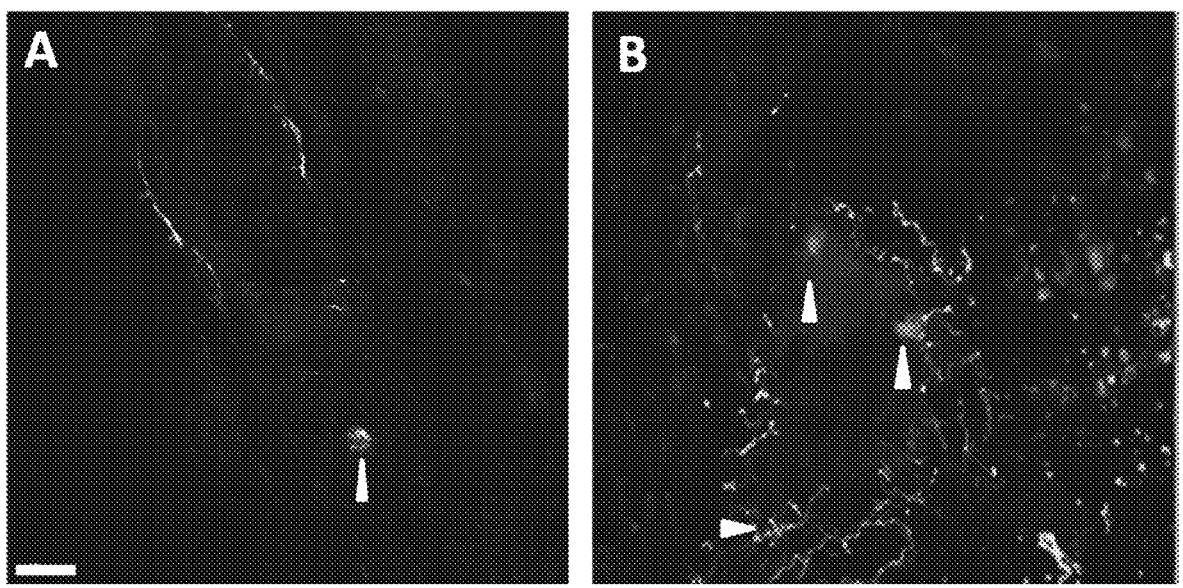
FIG. 13: α-bungarotoxin and beta III tubulin staining shows presence of motor endplates and significant innervation of the engineered muscle constructs after 6 months. A: MSC-oligomer constructs showed a lesser degree of innervation B. MEE-oligomer constructs showed robust innervation and motor endplate expression (arrowheads). Scale Bar=10 μm
Figure 14A:
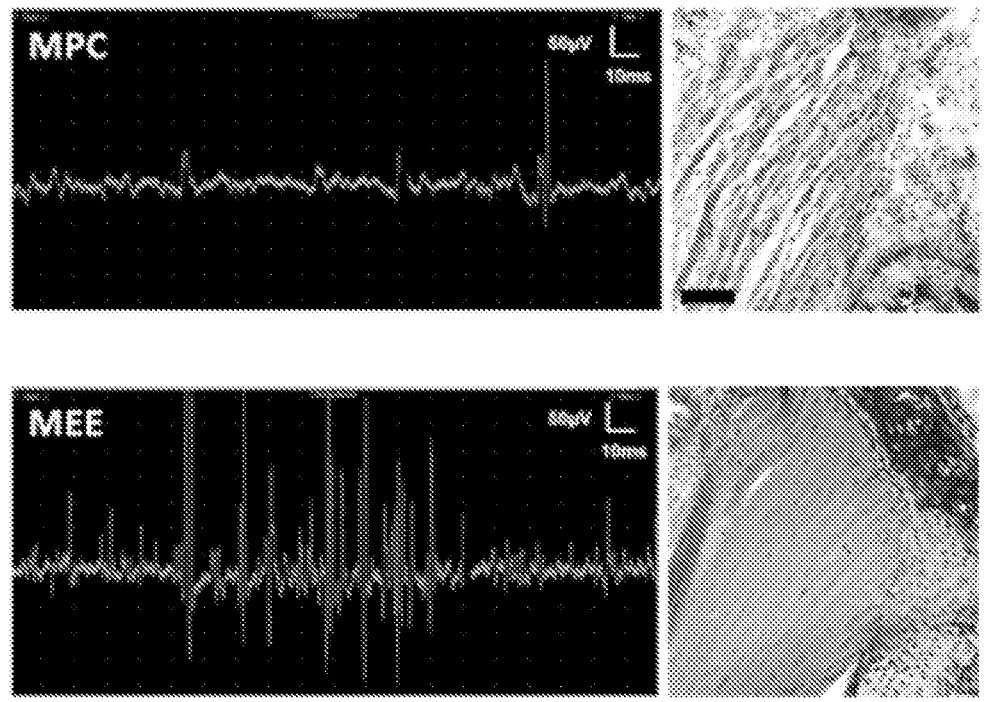
FIG. 14A: Animals with injured recurrent laryngeal nerves (RLN) treated with MEE-oligomer constructs showed increased EMG activity and myofiber diameter compared to MPC-oligomer implants. EMG of the adductor muscle complex showed increased activity in MEE-oligomer (C) treated animals compared to MPC-oligomer (A) treated animals. Histology showed some muscle atrophy in MPC-oligomer (B) treated animals and near normal myofiber architecture in MEE-oligomer (D) treated animals. Myofiber diameter of adductor muscle (E) showed significant increase in MEE-oligomer treated animals (Mean+/−SD, $p<0.001$, 2 animals per group, minimum 36 measurements per animal). Scale bar=100 μm.
Figure 14B:
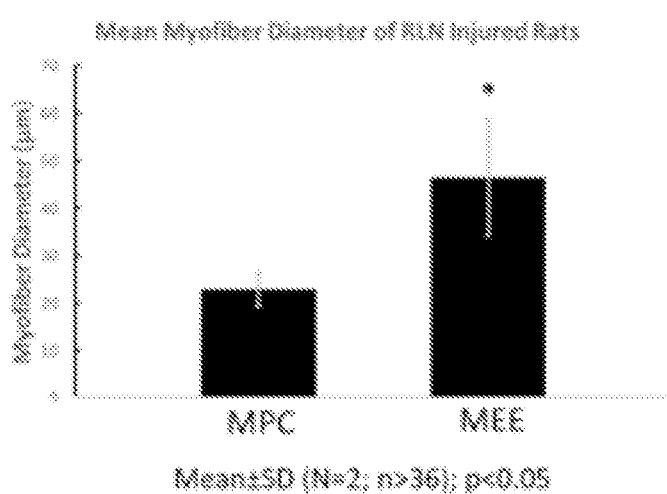
FIG. 14B: Bar graph illustrating mean myofiber diameter of adductor muscle following hemilaryngeal reconstruction within RLN injured rats with MPC-oligomer constructs or MEE-oligomer constructs.

Example 15: Reconstruction of Denervated Hemilarynx after Partial Laryngectomy with Engineered Cartilage and Muscle Constructs Yields Myogenesis, Neurovascular Regeneration, and Functional Tissue Restoration in Absence of an Inflammatory-Mediated Foreign Body Response Laryngectomy in the presence and absence of recurrent laryngeal nerve injury and implantation of engineered muscle and cartilage as described in Example 11. All animals survived the post-surgical period with no life-threatening complications. Some RLN injured animals showed mild stridor but this resolved with time. All animals steadily gained weight over the study period. Post-mortem gross pathological exam showed integration of the cartilage and muscle implants into host tissue with no macroscopic signs of inflammation. Alcian blue staining of cryo-sectioned specimens was weakly positive at 1 month (FIG. 11B). At 3 and 6 month timepoints, sections demonstrated progressive increase in Alcian blue staining consistent with glycosaminoglycan deposition and cartilage formation (FIG. 11C-D). H&E staining at 1 month displayed immature muscle neighboring native adductor muscle with no foreign body response (FIG. 12A,D). At 3 months, maturation of the muscle within the implant was demonstrated by development of cross striations and myofiber alignment (FIG. 12B, E). By 6 months, little to no immature muscle was visible within the defect area suggesting complete integration with nature tissue (FIG. 12C-F).

α-bungarotoxin and beta III tubulin staining demonstrated that implants that were induced to form motor endplates (MEE) showed a great number of motor endplates and robust innervation (FIG. 13). Qualitative EMG measurements of the adductor muscle complex of the MPC-oligomer treated animals showed low level activity (FIG. 14A,B) whereas the MEE-oligomer treated animals showed near normal muscle activity, with interference and recruitment patterns (during laryngospasm) that mimicked normal adductor muscle (FIG. 14C,D). This finding was further corroborated by adductor muscle complex myofiber diameter measurements, with values for MEE-oligomer treated animals significantly greater than those for MPC-oligomer treated animals (p<0.001 FIG. 14E).

Figure 15:
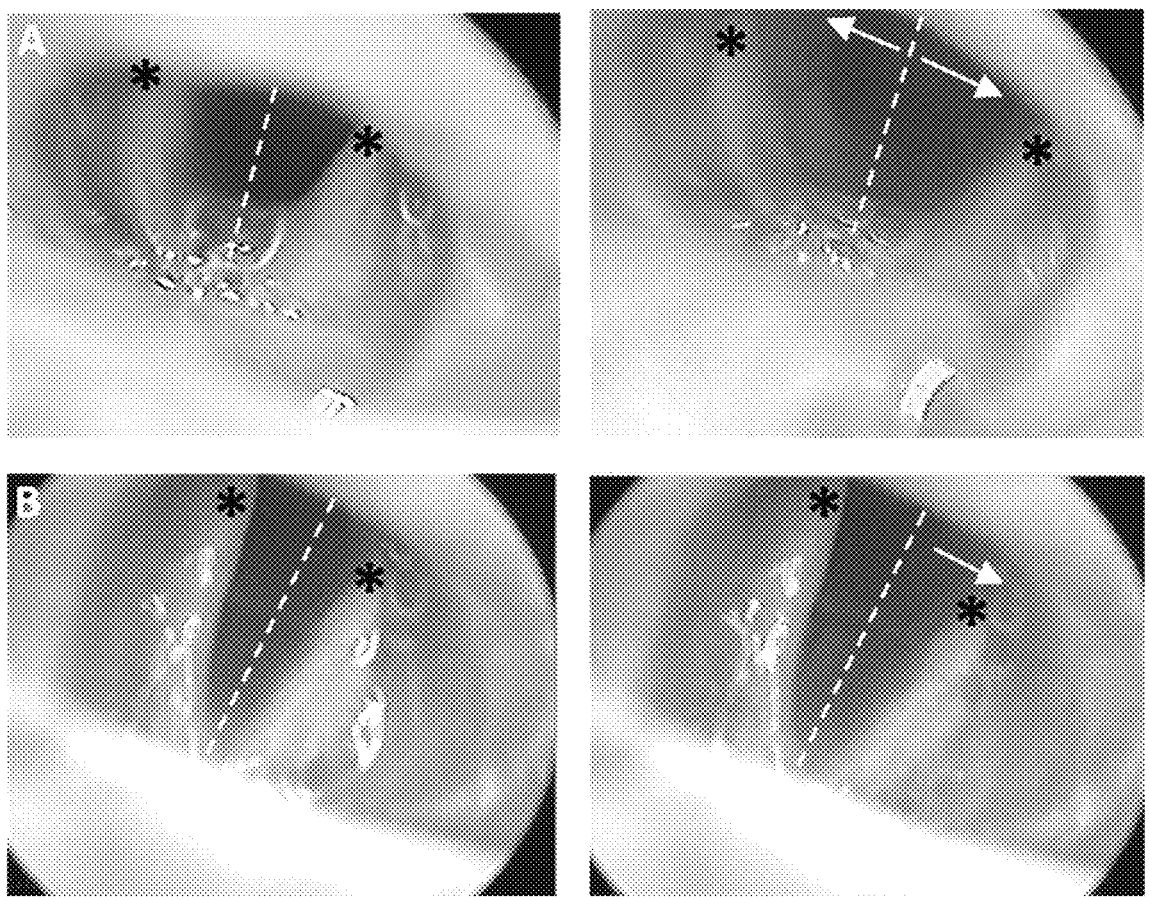
FIG. 15: Still images from video laryngoscopy obtained 3 months after hemilaryngeal reconstruction in rat laryngectomy model with recurrent laryngeal nerve injury. Recovery of left vocal fold movement was observed in animals treated with MEE-oligomer constructs (A). Animals treated with the MSC-oligomer constructs (B) showed less pronounced movement in the left vocal fold.

In nerve injured animals, video laryngoscopy showed function recovery in 100% of animals receiving the MEE implant with definitive although slightly delayed movement at all timepoints. By contrast, none of the animals receiving the MPC implant showed definitive movement at any timepoint (FIG. 15).

REFERENCES

1. Howlader N, Noone A M, Krapcho M, Miller D, Bishop K, Altekruse S F, Kosary C L, Yu M, Ruhl J, Tatalovich Z, Mariotto A, Lewis D R, Chen H S, Feuer E J, Cronin K A (eds). SEER Cancer Statistics Review, 1975-2013, National Cancer Institute. Bethesda, Md., http://seer.cancer.gov/csr/1975_2013/, based on November 2015 SEER data submission, posted to the SEER web site, April 2016.

Bian W, Bursac N. Tissue engineering of functional skeletal muscle: challenges and recent advances. IEEE Eng Med Biol Mag 2008; 27:109-113.

Mertens J P, Sugg K B, Lee J D, Larkin L M. Engineering muscle constructs for the creation of functional engineered musculoskeletal tissue. Regen Med 2014; 9:89-100.

Gillies A R, Lieber R L. Structure and function of the skeletal muscle extracellular matrix. Muscle Nerve 2011; 44:318-331.

Cheng C S, Davis B N, Madden L, Bursac N, Truskey G A. Physiology and metabolism of tissue-engineered skeletal muscle. Exp Biol Med (Maywood) 2014; 239:1203-1214.

Ostrovidov S, Hosseini V, Ahadian S et al. Skeletal muscle tissue engineering: methods to form skeletal myotubes and their applications. Tissue Eng Part B Rev 2014; 20:403-436.

2. Halum S L, Bijangi-Vishehsaraei K, Zhang H, Sowinski J, Bottino M C. Stem cell-derived tissue-engineered constructs for hemilaryngeal reconstruction. Ann Otol Rhinol Laryngol 2014; 123:124-134.

3. Morehead J M, Holt G R. Soft-tissue response to synthetic biomaterials. Otolaryngol Clin North Am 1994; 27:195-201.

4. Porzionato A, Sfriso M M, Pontini A et al. Decellularized Human Skeletal Muscle as Biologic Scaffold for Reconstructive Surgery. Int J Mol Sci 2015; 16:14808-14831.

5. Hinds S, Bian W, Dennis R G, Bursac N. The role of extracellular matrix composition in structure and function of bioengineered skeletal muscle. Biomaterials 2011; 32:3575-3583.

6. Rhim C, Lowell D A, Reedy M C et al. Morphology and ultrastructure of differentiating three-dimensional mammalian skeletal muscle in a collagen gel. Muscle Nerve 2007; 36:71-80.

7. Rossi C A, Pozzobon M, Ditadi A et al. Clonal characterization of rat muscle satellite cells: proliferation, metabolism and differentiation define an intrinsic heterogeneity. PLoS One 2010; 5:e8523.

8. Huang Y C, Dennis R G, Larkin L, Baar K. Rapid formation of functional muscle in vitro using fibrin gels. J Appl Physiol (1985) 2005; 98:706-713.

9. Powell C A, Smiley B L, Mills J, Vandenburgh H H. Mechanical stimulation improves tissue-engineered human skeletal muscle. Am J Physiol Cell Physiol 2002; 283:C1557-1565.

10. Kreger S T, Bell B J, Bailey J et al. Polymerization and matrix physical properties as important design considerations for soluble collagen formulations. Biopolymers 2010; 93:690-707.

11. Bailey J L, Critser P J, Whittington C, Kuske J L, Yoder M C, Voytik-Harbin S L. Collagen oligomers modulate physical and biological properties of three-dimensional self-assembled matrices. Biopolymers 2011; 95:77-93.

12. Blum K M, Novak T, Watkins L, Neu C P, Wallace J M, Bart Z R, Voytik-Harbin S L. Acellular and cellular high-density, collagen-fibril constructs with suprafibrillar organization. Biomater Sci 2016; 4:711-723.

13. Voytik-Harbin S L, Han B. Collagen-cell interactions and modeling in microenvironments. In: Neu C P, Genin G, eds. CRC Handbook of Imaging in Biological Mechanics. Boca Raton, Fla.: Taylor & Francis Group; 2015:261-273.

Whittington C F, Yoder M C, Voytik-Harbin S L. Collagen-polymer guidance of vessel network formation and stabilization by endothelial colony forming cells in vitro. Macromol Biosci 2013; 13:1135-1149.

Critser P J, Kreger S T, Voytik-Harbin S L, Yoder M C. Collagen matrix physical properties modulate endothelial colony forming cell-derived vessels in vivo. Microvasc Res 2010; 80:23-30.

14. Yrineo A A, Adelsperger A R, Durkes A C et al. Murine ultrasound-guided transabdominal para-aortic injections of self-assembling type I collagen oligomers. J Control Release 2017; 249:53-62.

15. ASTM Standard F3089: Characterization and Standardization of Polymerizable Collagen-Based Products and Associated Collagen—Cell Interactions; ASTM International: West Conshohocken, Pa., 2014; DOI: 10.1520/F3089-14; www.astm.org.

16. Brookes S, Voytik-Harbin S, Zhang H, and Halum S. Three-dimensional tissue-engineered skeletal muscle for laryngeal reconstruction. The Laryngoscope 2018; 128: 603-609.

17. Suzuki H, Araki K, Matsui T, Tomifuji M, Tamashita T, Kobayashi Y and Shiotani A. Value of a novel PGA-collagen tube on recurrent laryngeal nerve regeneration in a rat model. The Laryngoscope 2016; 126:E233-E239.

We claim:

1. A collagen composition comprising a synthetic fibrillar collagen network having a uniform density of aligned polymerized oligomeric collagen fibrils throughout said network.

2. The collagen composition of claim 1 further comprising cells.

3. The collagen composition of claim 2, wherein the cells are stem cells, progenitor cells, motor endplate-expressing muscle progenitor cells, or a combination thereof.

4. The collagen composition of claim 2, wherein the cells are muscle, skeletal muscle, nerve, tendon, or ligament cells.

5. A tissue implant for human or veterinary use comprising the collagen composition of claim 2.

6. The collagen composition of claim 2, wherein the cells are embedded within the fibrillar collagen network.

7. A tissue implant for human or veterinary use comprising the collagen composition of claim 6.

8. The tissue implant of claim 7, wherein the tissue implant comprises muscle, skeletal muscle, nerve, tendon, or ligament cells.

9. The tissue implant of claim 7, wherein the cells are one or more of muscle progenitor cells, motor endplate-expressing muscle progenitor cells, or adipose-derived stem cells.

10. The collagen composition of claim 6, wherein the cells are muscle, skeletal muscle, nerve, tendon, or ligament cells.

11. The collagen composition of claim 1, wherein the polymerized oligomeric collagen fibrils consist of Type I oligomeric collagen.

12. A tissue implant for human or veterinary use comprising the collagen composition of claim 1.

13. A synthetic fibrillar collagen network, having a uniform density of aligned polymerized oligomeric collagen fibrils, said network prepared by a process comprising extruding a polymerizable oligomeric collagen solution under conditions permissive to polymerization of the oligomeric collagen to form said fibrillar collagen network having a uniform density of polymerized oligomeric collagen fibrils throughout said network, wherein the polymerized oligomeric collagen fibrils are aligned.

14. The synthetic fibrillar collagen network of claim 13, wherein the polymerizable oligomeric collagen solution further comprises cells, and said cells are attached to said fibrillar collagen network.

15. The synthetic fibrillar collagen network of claim 14, wherein the cells are stem cells, progenitor cells, motor endplate-expressing muscle progenitor cells, or a combination thereof.

16. A process comprising extruding a polymerizable oligomeric collagen solution to form a solid collagen construct wherein the solid collagen construct comprises a uniform density of aligned collagen fibrils.

17. The process of claim 16, wherein the polymerizable oligomeric collagen solution further comprises cells.

18. The process of claim 17, wherein the cells are stem cells, progenitor cells, motor-endplate expressing muscle progenitor cells, or a combination thereof.

* * * * *